(12) United States Patent
Corredor et al.

(10) Patent No.: US 11,361,434 B2
(45) Date of Patent: Jun. 14, 2022

(54) MACHINE LEARNING FOR OTITIS MEDIA DIAGNOSIS

(71) Applicant: OtoNexus Medical Technologies, Inc., Seattle, WA (US)

(72) Inventors: Charlie Corredor, Seattle, WA (US); Mark A Moehring, Seattle, WA (US); Caitlin Cameron, Mercer Island, WA (US); George A. Gates, Seattle, WA (US)

(73) Assignee: OTONEXUS MEDICAL TECHNOLOGIES, INC., Bellevue, WA (US)

( * ) Notice: Subject to any disclaimer, the term of this patent is extended or adjusted under 35 U.S.C. 154(b) by 137 days.

(21) Appl. No.: 16/752,220

(22) Filed: Jan. 24, 2020

(65) Prior Publication Data

US 2020/0286227 A1   Sep. 10, 2020

Related U.S. Application Data

(60) Provisional application No. 62/796,762, filed on Jan. 25, 2019.

(51) Int. Cl.
*G06T 7/00* (2017.01)
*G06N 20/10* (2019.01)
(Continued)

(52) U.S. Cl.
CPC .......... *G06T 7/0012* (2013.01); *G06K 9/6223* (2013.01); *G06K 9/6267* (2013.01);
(Continued)

(58) Field of Classification Search
CPC ......... G06T 7/0012; G06T 2207/10048; G06T 2207/10101; G06T 2207/10132;
(Continued)

(56) References Cited

U.S. PATENT DOCUMENTS 5,235,510 A   8/1993   Yamada et al.
5,331,550 A   7/1994   Stafford et al.
(Continued)

FOREIGN PATENT DOCUMENTS

WO   WO-0010451 A1   3/2000
WO   WO-0126026 A2   4/2001
(Continued)

OTHER PUBLICATIONS

Chan et al.,"Detecting middle ear fluid using smartphones," Sci. Transl. Med. 11, pp. 1-9, eaav1102 (2019).
(Continued)

*Primary Examiner* — John B Strege
(74) *Attorney, Agent, or Firm* — Wilson Sonsini Goodrich & Rosati

(57) ABSTRACT

Disclosed herein are systems and methods for classifying a tympanic membrane by using a classifier. The classifier is a machine learning algorithm. A method for classifying a tympanic membrane includes steps of: receiving, from an interrogation system, one or more datasets relating to the tympanic membrane; determining a set of parameters from the one or more datasets, wherein at least one parameter of the set of parameters is related to a dynamic property or a static position of the tympanic membrane; and outputting a classification of the tympanic membrane based on a classifier model derived from the set of parameters. The classification comprises one or more of a state, a condition, or a mobility metric of the tympanic membrane.

21 Claims, 10 Drawing Sheets

(51) Int. Cl.
  *G06K 9/62* (2022.01)
  *G06N 3/08* (2006.01)
(52) U.S. Cl.
  CPC ............ *G06N 3/088* (2013.01); *G06N 20/10* (2019.01); *G06T 2207/10048* (2013.01); *G06T 2207/10101* (2013.01); *G06T 2207/10132* (2013.01); *G06T 2207/20081* (2013.01); *G06T 2207/20084* (2013.01)
(58) Field of Classification Search
  CPC ...... G06T 2207/20081; G06T 2207/20; G06N 20/10; G06N 3/088; G06K 9/6223; G06K 9/6267; A61B 5/12; A61B 1/227; A61B 1/00; A61B 1/06
  See application file for complete search history.

(56) References Cited

U.S. PATENT DOCUMENTS

| | | | |
|---|---|---|---|
| 6,090,044 A * | 7/2000 | Bishop | G16H 15/00 600/300 |
| 7,058,441 B2 | 6/2006 | Shahar et al. | |
| 7,283,653 B2 | 10/2007 | Zahlmann et al. | |
| 7,771,356 B2 | 8/2010 | Voie et al. | |
| 8,115,934 B2 | 2/2012 | Boppart et al. | |
| 8,798,345 B2 | 8/2014 | Sasaki et al. | |
| 8,996,098 B2 | 3/2015 | Spector | |
| 9,053,536 B2 | 6/2015 | Imamura et al. | |
| 9,445,713 B2 | 9/2016 | Douglas et al. | |
| 9,536,054 B1 | 1/2017 | Podilchuk et al. | |
| 9,589,374 B1 | 3/2017 | Gao et al. | |
| 9,636,007 B2 | 5/2017 | Hoberman et al. | |
| 9,684,960 B2 | 6/2017 | Buzaglo et al. | |
| 9,750,450 B2 | 9/2017 | Shie et al. | |
| 9,867,528 B1 | 1/2018 | Boppart et al. | |
| 9,922,242 B2 | 3/2018 | Eineren et al. | |
| 10,013,757 B2 | 7/2018 | Kim et al. | |
| 2002/0026125 A1 * | 2/2002 | Leysieffer | A61B 5/121 600/559 |
| 2003/0026470 A1 | 2/2003 | Kasai | |
| 2004/0068167 A1 | 4/2004 | Hsieh et al. | |
| 2004/0249259 A1 | 12/2004 | Heimdal et al. | |
| 2006/0235725 A1 | 10/2006 | Kleen et al. | |
| 2006/0282009 A1 | 12/2006 | Oberg et al. | |
| 2007/0112273 A1 | 5/2007 | Rogers | |
| 2007/0129632 A1 | 6/2007 | Voie et al. | |
| 2009/0112100 A1 | 4/2009 | Shioi | |
| 2011/0099133 A1 | 4/2011 | Chang et al. | |
| 2012/0185275 A1 | 7/2012 | Loghmani | |
| 2013/0303941 A1 | 11/2013 | Porges et al. | |
| 2014/0036054 A1 | 2/2014 | Zouridakis | |
| 2014/0249426 A1 * | 9/2014 | Huh | A61B 5/0507 600/473 |
| 2015/0065803 A1 | 3/2015 | Douglas et al. | |
| 2015/0305609 A1 * | 10/2015 | Hoberman | A61B 1/227 382/128 |
| 2017/0014053 A1 * | 1/2017 | Moehring | A61B 8/12 |
| 2017/0071509 A1 | 3/2017 | Pandey et al. | |
| 2017/0126943 A1 | 5/2017 | Fletcher et al. | |
| 2017/0132367 A1 | 5/2017 | Cheng et al. | |
| 2017/0209078 A1 | 7/2017 | Hoberman et al. | |
| 2017/0323176 A1 * | 11/2017 | Lo | G06F 16/58 |
| 2017/0360302 A1 | 12/2017 | Chesavage et al. | |
| 2018/0025210 A1 | 1/2018 | Remiszewski et al. | |
| 2018/0211380 A1 | 7/2018 | Tandon et al. | |
| 2018/0242860 A1 | 8/2018 | Leboeuf et al. | |
| 2018/0260616 A1 | 9/2018 | Spinoulas et al. | |
| 2018/0310917 A1 | 11/2018 | Moehring et al. | |
| 2019/0200873 A1 | 7/2019 | Chesavage et al. | |
| 2019/0216308 A1 * | 7/2019 | Senaras | A61B 1/00009 |
| 2019/0365292 A1 | 12/2019 | Moehring et al. | |
| 2020/0037930 A1 * | 2/2020 | Abramoff | G16H 50/30 |

FOREIGN PATENT DOCUMENTS

| | | |
|---|---|---|
| WO | WO-2009157825 A1 | 12/2009 |
| WO | WO-2013160780 A1 | 10/2013 |
| WO | WO-2018045269 A1 | 3/2018 |
| WO | WO-2018106005 A1 | 6/2018 |
| WO | WO-2018140014 A1 | 8/2018 |
| WO | WO-2018198253 A1 | 11/2018 |
| WO | WO-2018222782 A1 | 12/2018 |

OTHER PUBLICATIONS

Kasher, M.S., "Otitis Media Analysis: An Automated Feature Extraction and Image Classification System," Helsinki Metropolia University of Applied Sciences, Bachelor of Engineering, Degree Programme in Electronics, Bachelor's Thesis (Apr. 25, 2018).

Kuruvilla, A. et al., "Automated diagnosis of otitis media: vocabulary and grammar," International Journal of Biomedical Imaging: NA. Hindawl Limited. pp. 1-15 (2013).

Myburgh et al. Otitis media diagnosis for developing countries using tympanic membrane image-analysis. EBioMedicine 5 (2016) 156-160.

Myburgh, H. et al., "Towards low cost automated smartphone- and cloud-based otitis media diagnosis," Biomedical Signal Processing and Control 39 (2018) 34-52.

Shie, C.K. et al., "A hybrid feature-based segmentation and classification system for the computer aided self-diagnosis of otitis media," Conf Proc IEEE Eng Med Biol Soc., 2014; 2014:4655-8.

Somrak, M. et al., "Tricorder: consumer medical device for discovering common medical conditions," Informatica 38.1: 81-88, Slovenian Society Informatika. (Mar. 2014).

PCT/US2020/015101 Search Report & Written Opinion dated Apr. 9, 2020.

Rappaport, K. et al., "Comparative Assessment of a Smartphone Otoscope for the Diagnosis and Management of Acute Otitis Media," Provisional Section on Advances in Therapeutics and Technology Poster Presentation (Oct. 28, 2013).

Senaras, C. et al, "Detection of eardrum abnormalities using ensemble deep learning approaches," Proc. SPIE 10575, Medical Imaging 2018: Computer-Aided Diagnosis, 105751A (Feb. 27, 2018).

Shaikh, N. et al., "Development of an algorithm for the diagnosis of otitis media," Academic Pediatrics, vol. 12, Nos. 3, 214-218 (May-Jun. 2012).

Tran, T. et al., "Development of an Automatic Diagnostic Algorithm for Pediatric Otitis Media," Otology & neurotology : official publication of the American Otological Society, American Neurotology Society [and] European Academy of Otology and Neurotology 39.8: 1060-1065. (Sep. 2018).

Umea University "Diagnosing ear infection using smartphone." ScienceDaily. ScienceDaily, Mar. 30, 2016. (http://www.sciencedaily.com/releases/2016/03/160330102850.htm).

Vertan, C. et al., "Eardrum color content analysis in video-otoscopy images for the diagnosis support of pediatric," Int. Symp. on Signals, Circuits and Systems, Bucharest, Romania, Jul. 2011, pp. 1-4.

* cited by examiner

MACHINE LEARNING FOR OTITIS MEDIA DIAGNOSIS

CROSS-REFERENCE

This application claims the benefit of U.S. Provisional Application No. 62/796,762, filed Jan. 25, 2019, which application is incorporated herein by reference.

BACKGROUND

The present disclosure relates to systems and methods for characterizing tissue and related materials, such as for diagnosis. In particular, the present disclosure relates to measuring tissue mobility or position, such as mobility or position of the tympanic membrane for diagnosing and characterizing otitis media (i.e., ear infection). Embodiments of the present disclosure involve machine learning, for example, with a set of training data comprised of optical and/or acoustic and/or pressure datasets of tympanic membranes to predict tympanic membrane mobility or position. Prediction models may be generated with the training set and used to characterize the mobility or position a patient's tympanic membrane to thereby diagnose and characterize any otitis media.

Otitis media (OM) is a group of inflammatory diseases of the inner ear and the cause of the most prevalent childhood healthcare issue, commonly known as an "ear infection". OM is defined by the presence of a liquid effusion in the middle ear and consists of two main types: acute otitis media (AOM), otitis media with effusion (OME), Chronic otitis media (COM) and Chronic suppurative otitis media (CSOM). Rapid onset of infections that usually present with ear pain are characteristic of AOM middle ear effusions (MEE), while OME is not typically associated with symptoms because the MEE fluids are non-infectious.

Diagnosis of OM most commonly relies on otoscopy to visually assess the tympanic membrane (TM), i.e., the "ear drum". Otoscopes illuminate and magnify the TM to allow the physician to qualitatively interpret visual indicators related to OM infection, such as the coloration, transparency, and bulge. However, the accuracy of OME diagnosis by otoscopy varies due to the equipment and skills of the physician—pediatricians and otolaryngologists intimately familiar with OM have an estimated diagnostic accuracy in the range of 50-70% using otoscopy. Given the difficulty in properly diagnosing OM through otoscopy, only 40% of primary pediatricians are confident about their otoscopic findings and AOM is frequently misdiagnosed.

Accordingly, improved systems, devices, and methods for classifying a tympanic membrane and/or diagnosing otitis media are desired.

References which may be relevant to the disclosure herein may include U.S. Pat. Nos. 5,235,510, 5,331,550, 6,090,044, 7,058,441, 7,283,653, 7,771,356, 8,115,934, 8,798,345, 8,996,098, 9,053,536, 9,445,713, 9,536,054, 9,589,374, 9,636,007, 9,684,960, 9,750,450, 9,867,528, 9,922,242, and U.S. Ser. No. 10/013,757; U.S. Publications US2003026470, US2004068167, US2006235725, US2006282009, US2007112273, US2009112100, US2012185275, US2013303941, US2014036054, US2017071509, US2017126943, US2017132367, US2018025210, US2018211380, US2018242860, and US2018260616; and International Publications WO2000/010451, WO2001/026026, WO2009/157825, WO2018/045269, WO2018/106005, WO2018/140014, and WO2018/198253.

The following non-patent publications may be relevant to the disclosure herein: Vertan, C. et al, "Eardrum color content analysis in video-otoscopy images for the diagnosis support of pediatric," Int. Symp. on Signals, Circuits and Systems, Bucharest, Romania, July 2011; Shaikh, N. et al., "Development of an algorithm for the diagnosis of otitis media," Academic Pediatrics, Volume 12, Number 3 (May-June 2012); Kuruvilla, A. et al., "Automated diagnosis of otitis media: vocabulary and grammar," International Journal of Biomedical Imaging: NA. Hindawl Limited. (2013); Rappaport, K. et al., "Comparative Assessment of a Smartphone Otoscope for the Diagnosis and Management of Acute Otitis Media," Provisional Section on Advances in Therapeutics and Technology Poster Presentation (Oct. 28, 2013); Shie, C. K. et al., "A hybrid feature-based segmentation and classification system for the computer aided self-diagnosis of otitis media," Conf Proc IEEE Eng Med Biol Soc., 2014; 2014:4655-8; Somrak, M. et al., "Tricorder: consumer medical device for discovering common medical conditions," Informatica 38.1: 81(8). Slovenian Society Informatika. (March 2014); Myburgh, H. et al., "Towards low cost automated smartphone- and cloud-based otitis media diagnosis," Biomedical Signal Processing and Control 39 (2018) 34-52; Umea University. "Diagnosing ear infection using smartphone." ScienceDaily. ScienceDaily, 30 Mar. 2016. <www.sciencedaily.com/releases/2016/03/160330102850.htm>; Senaras, C. et al, "Detection of eardrum abnormalities using ensemble deep learning approaches," Proc. SPIE 10575, Medical Imaging 2018: Computer-Aided Diagnosis, 105751A (27 Feb. 2018); Kasher, M. S., "Otitis Media Analysis: An Automated Feature Extraction and Image Classification System," Helsink Metropolia University of Applied Sciences, Bachelor of Engineering, Degree Programme in Electronics, Bachelor's Thesis (25 Apr. 2018); and Tran, T. et al., "Development of an Automatic Diagnostic Algorithm for Pediatric Otitis Media," Otology & neurotology: official publication of the American Otological Society, American Neurotology Society [and] European Academy of Otology and Neurotology 39.8: 1060-1065. (September 2018).

SUMMARY

The present disclosure relates to systems and methods for measuring mobility and position of the tympanic membrane for diagnosing and characterizing otitis media (i.e., ear infection). Machine learning may be used with a set of training data comprised of optical and/or ultrasound and/or pressure datasets of tympanic membranes to generate a predictive model for tympanic membrane mobility and/or position.

Aspects of the present disclosure provide a method for classifying a tympanic membrane. The method may comprise: receiving, from an interrogation system, one or more datasets relating to the tympanic membrane; determining a set of parameters from the one or more datasets, wherein at least one parameter of the set of parameters is related to a dynamic property or a static position of the tympanic membrane; and outputting a classification of the tympanic membrane based on a classifier model derived from the set of parameters, wherein the classification comprises one or more of a state, a condition, or a mobility metric of the tympanic membrane.

In some embodiments, the interrogation system comprises an imaging system, and wherein the one or more datasets comprises one or more images of the tympanic membrane. In some embodiments, the classifier model comprises a machine learning algorithm. In some embodiments, the machine learning algorithm comprises one or more of linear regressions, logistic regressions, classification and regression tree algorithms, support vector machines (SVMs), naive Bayes, K-nearest neighbors, random forest algorithms, boosted algorithms such as XGBoost and LightGBM, neural networks, convolutional neural networks, and recurrent neural networks. In some embodiments, the machine learning algorithm is a supervised learning algorithm, an unsupervised learning algorithm, or a semi-supervised learning algorithm.

In some embodiments, the one or more images of the tympanic membrane comprises one or more ultrasound images. In some embodiments, the one or more ultrasound images comprise images from a pneumatic ultrasound tympanoscope. In some embodiments, the one or more ultrasound images are measured in response to a pneumatic excitation. In some embodiments, the one or more images of the tympanic membrane comprise one or more optical coherence tomography images. In some embodiments, the images comprise optical images.

In some embodiments, the at least one parameter related to the dynamic property or a static position of the membrane is in response to a pneumatic excitation. In some embodiments, the pneumatic excitation comprises a puff of gas. In some embodiments, the pneumatic excitation has a frequency greater than 10 Hz. In some embodiments, the dynamic property of the tympanic membrane comprises one or more of: an indication of a membrane movement or a membrane mobility; a minimum or maximum displacement of the tympanic membrane; an outlier displacement; a difference or a ratio between a minimum and a maximum displacement; a slope of a displacement or a slope of a difference or a ratio between a minimum and a maximum displacement with respect to a pressure of a pneumatic excitation; a response of a measured pressure versus an applied pressure; a visual movement of the tympanic membrane in response to a pneumatic excitation; one or more statistical components generated from singular value decomposition, principal component analysis, and K-means clustering; and ultrasound pulse echo amplitude or ultrasound echo phase or a derivative thereof or a moving average thereof. In some embodiments, the dynamic property of the tympanic membrane is normalized with respect to a pressure of a pneumatic excitation.

In some embodiments, the method further comprises generating one or more of an ordinal readout, a categorical readout, or a continuous numeric output of the tympanic membrane mobility. In some embodiments, an ordinal readout comprises a numerical scale relating to a degree of membrane mobility. In some embodiments, the numerical scale comprises a 0 to 4+ classification. In some embodiments, a categorical readout comprises an indication of a degree of membrane mobility as at least one of highly mobile, moderately mobile, semi mobile, or non-mobile. In some embodiments, a categorical readout comprises a binary classification. In some embodiments, a continuous numeric output comprises one or more of a measurement membrane displacement, a speed of membrane movement, or a speed of membrane recovery.

In some embodiments, the state or condition of the tympanic membrane comprises one or more of acute otitis media, acute otitis media with effusion, middle ear effusion, chronic otitis media, chronic suppurative otitis media, a bacterial infection, a viral infection, no effusion, and an unknown classification.

In some embodiments, the one or more datasets comprise m-mode ultrasound datasets. In some embodiments, the one or more datasets comprise infrared images. In some embodiments, the one or more datasets comprises pneumatic datasets. In some embodiments, the one or more datasets comprises one or more optical images are taken in response to a pneumatic excitation. In some embodiments, the static position comprises a distended membrane or a retracted membrane.

In another aspect, the present disclosure provides a system for classifying a tympanic membrane. The system may comprise: a computing system comprising a memory, the memory comprising instructions for classifying the tympanic membrane, wherein the computing system is configured to execute the instructions to at least: receive from an interrogation system, one or more datasets relating to the tympanic membrane; determine a set of parameters from the one or more datasets, wherein at least one parameter of the set of parameters is related to a dynamic property or a static position of the tympanic membrane; and output a classification of the tympanic membrane based on a classifier model derived from the set of parameters, wherein the classification comprises a state, a condition, or a mobility metric of the tympanic membrane.

In some embodiments, the interrogation system comprises an imaging system, and wherein the one or more datasets comprises one or more images of the tympanic membrane. In some embodiments, the system additionally comprises a pneumatic ultrasound tympanoscope.

In some embodiments, the classifier model comprises a machine learning algorithm. In some embodiments, the machine learning algorithm comprises one or more of linear regressions, logistic regressions, classification and regression tree algorithms, support vector machines (SVMs), naive Bayes, K-nearest neighbors, random forest algorithms, boosted algorithms such as XGBoost and LightGBM, neural networks, convolutional neural networks, and recurrent neural networks. In some embodiments, the machine learning algorithm is a supervised learning algorithm, an unsupervised learning algorithm, or a semi-supervised learning algorithm.

In some embodiments, the one or more images of the tympanic membrane comprises one or more ultrasound images. In some embodiments, the one or more ultrasound images comprise images from a pneumatic ultrasound tympanoscope. In some embodiments, the one or more ultrasound images are measured in response to a pneumatic excitation. In some embodiments, the one or more images of the tympanic membrane comprise one or more optical coherence tomography images. In some embodiments, the images comprise optical images.

In some embodiments, the at least one parameter related to dynamic property or a static position of the membrane is in response to a pneumatic excitation. In some embodiments, the pneumatic excitation comprises a puff of gas. In some embodiments, the pneumatic excitation comprises a frequency greater than 10 Hz. In some embodiments, the dynamic property of the tympanic membrane comprises one or more of: an indication of a membrane movement or a membrane mobility; a minimum or maximum displacement of the tympanic membrane; an outlier displacement; a difference or a ratio between a minimum and a maximum displacement; a slope of a displacement or a slope of a difference or a ratio between a minimum and a maximum displacement with respect to a pressure of a pneumatic excitation; a response of a measured pressure versus an applied pressure; a visual movement of the tympanic membrane in response to a pneumatic excitation; one or more statistical components generated from singular value decomposition, principal component analysis, and K-means clustering; and ultrasound pulse echo amplitude or ultrasound echo phase or a derivative thereof or a moving average thereof. In some embodiments, the dynamic property of the tympanic membrane is normalized with respect to a pressure of a pneumatic excitation.

In some embodiments, the computing system is further configured to execute the instructions to generate one or more of an ordinal readout, a categorical readout, or a continuous numeric output of the tympanic membrane mobility. In some embodiments, an ordinal readout comprises a numerical scale relating to a degree of membrane mobility. In some embodiments, the numerical scale comprises a 0 to 4+ classification. In some embodiments, a categorical readout comprises an indication of a degree of membrane mobility as at least one of highly mobile, moderately mobile, semi mobile, or non-mobile. In some embodiments, a categorical readout comprises a binary classification. In some embodiments, a continuous numeric output comprises one or more of a measurement membrane displacement, a speed of membrane movement, or a speed of membrane recovery.

In some embodiments, the state or condition of the tympanic membrane comprises one or more of acute otitis media, acute otitis media with effusion, middle ear effusion, chronic otitis media, chronic suppurative otitis media, a bacterial infection, a viral infection, no effusion, and an unknown classification.

In some embodiments, the one or more datasets comprise m-mode ultrasound datasets. In some embodiments, the one or more datasets comprise infrared images. In some embodiments, the one or more datasets comprises pneumatic datasets. In some embodiments, the one or more datasets comprises one or more optical images are taken in response to a pneumatic excitation. In some embodiments, the static position comprises a distended membrane or a retracted membrane.

In another aspect, the present disclosure provides a non-transitory computer readable medium comprising machine-executable code that upon execution by a computing system implements a method for classifying a membrane, the method comprising: receiving from an interrogation system, one or more datasets relating to the tympanic membrane; determining a set of parameters from the one or more datasets, wherein at least one parameter of the set of parameters is related to a dynamic property or a static position of the tympanic membrane; and outputting a classification of the tympanic membrane based on a classifier model derived from the set of parameters, wherein the classification comprises a state, a condition, or a mobility metric of the tympanic membrane.

In some embodiments, the interrogation system comprises an imaging system, and wherein the one or more datasets comprises one or more images of the tympanic membrane. In some embodiments, the method further comprises the method of any aspect or embodiment disclosed herein.

In another aspect, a method of training a computer-implemented classifier is provided. The method may comprise: receiving a set of parameters based on one or more datasets relating to one or more tympanic membranes and one or more classified datasets relating to the one or more tympanic membranes, wherein the classification comprises a state, a condition, or a mobility metric of the tympanic membrane and wherein the set of parameters comprises at least one parameter related to a dynamic property or a static position of the one or more tympanic membranes; storing the set of parameters and the one or more classified datasets in a database; building a classifier model based on the set of parameters and the one or more classified datasets, wherein the classifier model is derived from the set of parameters and wherein the classifier model outputs a classification based on a dataset of the one or more classified datasets; and using the classifier model to provide a classification of an unclassified dataset.

In some embodiments, the method further comprises updating the database based on a second one or more classified datasets; and updating the classifier model based on the second one or more classified datasets. In some embodiments, the method further comprises using the classifier model to provide a classification of an unclassified dataset by the method for classifying a tympanic membrane of any aspect or embodiment.

In another aspect, a system for training a computer-implemented classifier is provided. The system may comprise: a computing system comprising a memory, the memory comprising instructions for training the dataset, wherein the computing system is configured to execute the instructions to at least: receive a set of parameters based on one or more datasets relating to one or more tympanic membranes and one or more classified datasets relating to the one or more tympanic membranes, wherein the classification comprises a state, a condition, or a mobility metric of the tympanic membrane and wherein the set of parameters comprises at least one parameter related to a dynamic property or a static position of the one or more tympanic membranes; store the set of parameters and the one or more classified datasets in a database; build a classifier model based on the set of parameters and the one or more classified datasets, wherein the classifier model is derived from the set of parameters and wherein the classifier model outputs a classification based on a dataset of the one or more classified datasets; and use the classifier model to provide a classification of an unclassified dataset.

In some embodiments, the system is configured to execute the instructions to at least: update the database based on a second one or more classified datasets; and update the classifier model based on the second one or more classified datasets. In some embodiments, the system further comprises the system for classifying a tympanic membrane of any aspect or embodiment.

In another aspect, the present disclosure provides a non-transitory computer readable medium comprising machine-executable code that upon execution by a computing system implements a method for training a computer-implemented classifier. The method may comprise: receiving a set of parameters based on one or more datasets relating to one or more tympanic membranes and one or more classified datasets relating to the one or more tympanic membranes, wherein the classification comprises a state, a condition, or a mobility metric of the tympanic membrane and wherein the set of parameters comprises at least one parameter related to a dynamic property or a static position of the one or more tympanic membranes; storing the set of parameters and the one or more classified datasets in a database; building a classifier model based on the set of parameters and the one or more classified datasets, wherein the classifier model is derived from the set of parameters and wherein the classifier model outputs a classification; and using the classifier model to provide a classification of an unclassified dataset.

In some embodiments, the method further comprises updating the database based on a second one or more classified datasets; and updating the classifier model based on the second one or more classified datasets. In some embodiments, the method further comprises using the classifier model to provide a classification of an unclassified datasets by the method for classifying a tympanic membrane of any aspect or embodiment.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

Figure 1:
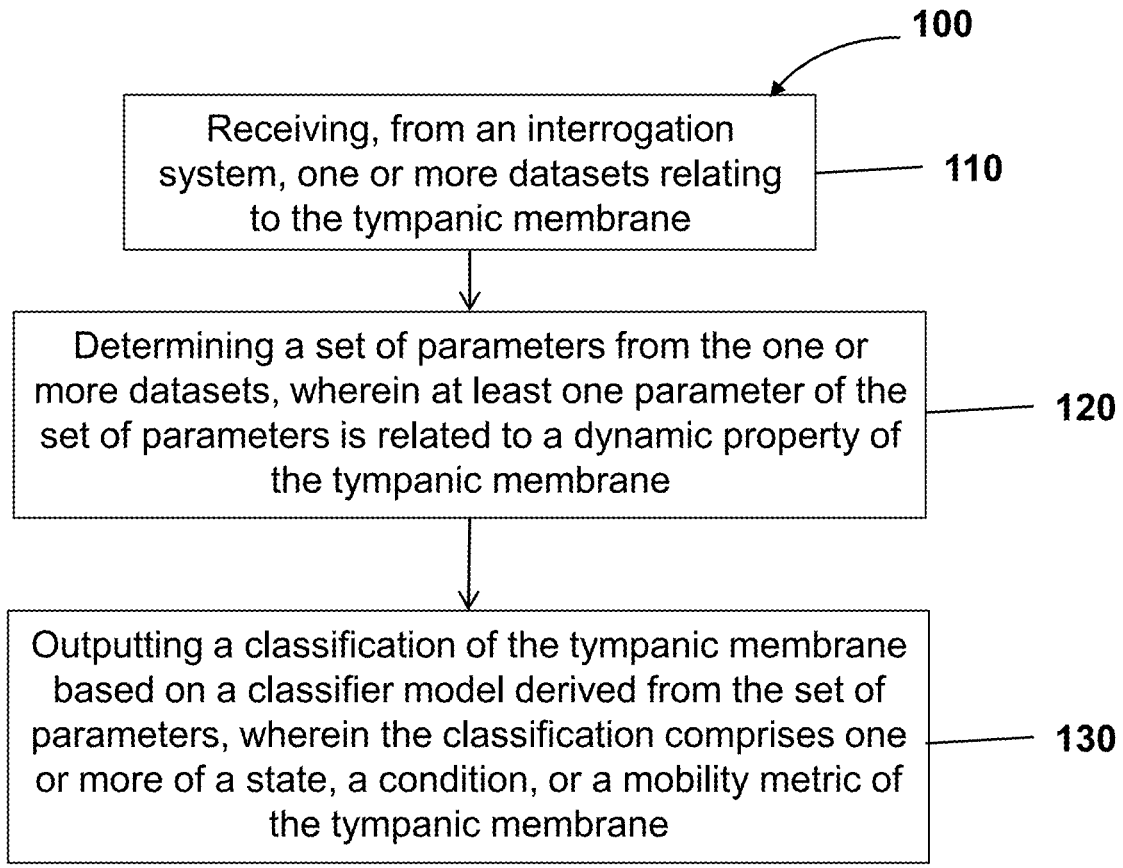
FIG. 1 is a flow chart of an example method of characterizing a tympanic membrane, in accordance with some embodiments.

The methods, systems, and media as disclosed herein may improve upon existing methods of classifying tissue by providing an improved classification (e.g., a diagnosis) of a tissue. For example, methods and systems provided herein may use machine learning methods to build a classifier which improves a classification of a tympanic membrane. A machine learning approach may leverage large datasets in order gain new insights into the datasets. The classifier model may improve characterization of a tympanic membrane which may lead to better patient outcomes. The classifier model may provide clinicians with information for more accurate otitis media management (e.g., tympanic membrane mobility information and/or a state or condition of the tympanic membrane) while reducing variance due to physician training and experience using pneumatic otoscopy. In some cases, the methods and systems provided herein may directly provide a disease state from a trained and validated algorithm.

The methods, systems, and media as disclosed herein may improve upon existing methods of classifying tissue by leveraging parameters related to a mobility of the tympanic membrane. The normal tympanic membrane may move in response to pressure, and a lack of or reduction in mobility is an indication of fluid in the middle ear, a perforation, or tympanosclerosis, etc. The addition of the mobility measurement may be important for diagnostic accuracy because the predictive value of visible eardrum characteristics for OM diagnosis can vary. Accordingly, the additional information of mobility may provide an indication of presence of effusion even when the appearance of the eardrum otherwise gives no indication of middle ear pathology.

The methods, systems, and media as disclosed herein may be used in combination with for example devices and methods to characterize a ductile membrane, surface, and sub-surface properties such as those described in commonly owned U.S. Pat. No. 7,771,356 and U.S. Patent Publication Nos. 2019/0365292, 2018/0310917, and 2017/0014053, each of which is incorporated by reference in their entireties. The methods, systems, and media as disclosed herein may be used in combination with for example devices and methods using optical coherence tomography (OCT), as disclosed in commonly assigned U.S. Patent Publication No. 2019/0200873 and U.S. Patent Publication No. 2017/0360302, each of which is incorporated herein by reference in its entirety.

The methods, systems, and media as disclosed herein may be used to characterize a number of biological tissues to provide a variety of diagnostic information. A biological tissue may comprise a patient organ. A speculum may be disposed within a bodily cavity to characterize a patient tissue. A patient organ or bodily cavity may comprise, for example, a muscle, a tendon, a ligament, a mouth, a tongue, a pharynx, an esophagus, a stomach, an intestine, an anus, a liver, a gallbladder, a pancreas, a nose, a larynx, a trachea, lungs, a kidneys, a bladder, a urethra, a uterus, a vagina, an ovary, a testicle, a prostate, a heart, an artery, a vein, a spleen, a gland, a brain, a spinal cord, a nerve, etc, to name a few.

The methods, systems, and media as disclosed herein may be used to classify a tympanic membrane. For example, a membrane may be classified to determine a condition of an ear, such as acute otitis media (AOM), chronic otitis media, otitis media with effusion and/or chronic suppurative otitis media. A classification that an ear exhibits AOM may include detection of the presence of effusion and characterization of the type of effusion as one of serous, mucoid, purulent, or combinations of these. In AOM, the middle ear effusion (MEE) may be induced by infective agents and may be thin or serous with viral infection and thicker and purulent with bacterial infection. Accordingly, determining various properties of a fluid adjacent a tympanic membrane may provide information which may be used to characterize a membrane.

Reference will now be made in detail to various embodiments, examples of which are illustrated in the accompanying drawings. In the following detailed description, numerous specific details are set forth in order to provide a thorough understanding of the present disclosure and the described embodiments. However, the embodiments of the present disclosure are optionally practiced without these specific details. In other instances, well-known methods, procedures, components, and circuits have not been described in detail so as not to unnecessarily obscure aspects of the embodiments. In the drawings, like reference numbers designate like or similar steps or components.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, the terms "comprises", "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "subject" and "patient" are used interchangeably. As used herein, the terms "subject" and "subjects" refers to an animal (e.g., birds, reptiles, and mammals), a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100.

FIG. 1 is a flow chart of an example method 100 for classifying a tympanic membrane, in accordance with some embodiments. At an operation 110, a method 100 may comprise receiving, from an interrogation system, one or more datasets relating to the tympanic membrane. At an operation 120, a method 100 may comprise determining a set of parameters from the one or more datasets. At least one parameter of the set of parameters may be related to a dynamic property of the tympanic membrane. At an operation 130, a method 100 may comprise outputting a classification of the tympanic membrane based on a classifier model derived from the set of parameters. The classification may comprise one or more of a state, a condition, or a mobility metric of the tympanic membrane.

Although the above operations show a method 100 of classifying a tympanic membrane, in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the method of manufacture.

One or more steps of the method 100 may be performed with the circuitry as described herein, for example, one or more of the digital processing device or processor or logic circuitry such as the programmable array logic for a field programmable gate array. The circuitry may be programmed to provide one or more steps of the method 100, and the program may comprise program instructions stored on a computer readable memory or programmed steps of the logic circuitry such as the programmable array logic or the field programmable gate array, for example. Embodiments, variations, and examples of a digital processing device operable to perform one or more steps of the method 100 is described elsewhere herein for example with respect to the section "Digital Processing Device" and FIG. 10 described therein.

Figure 2:
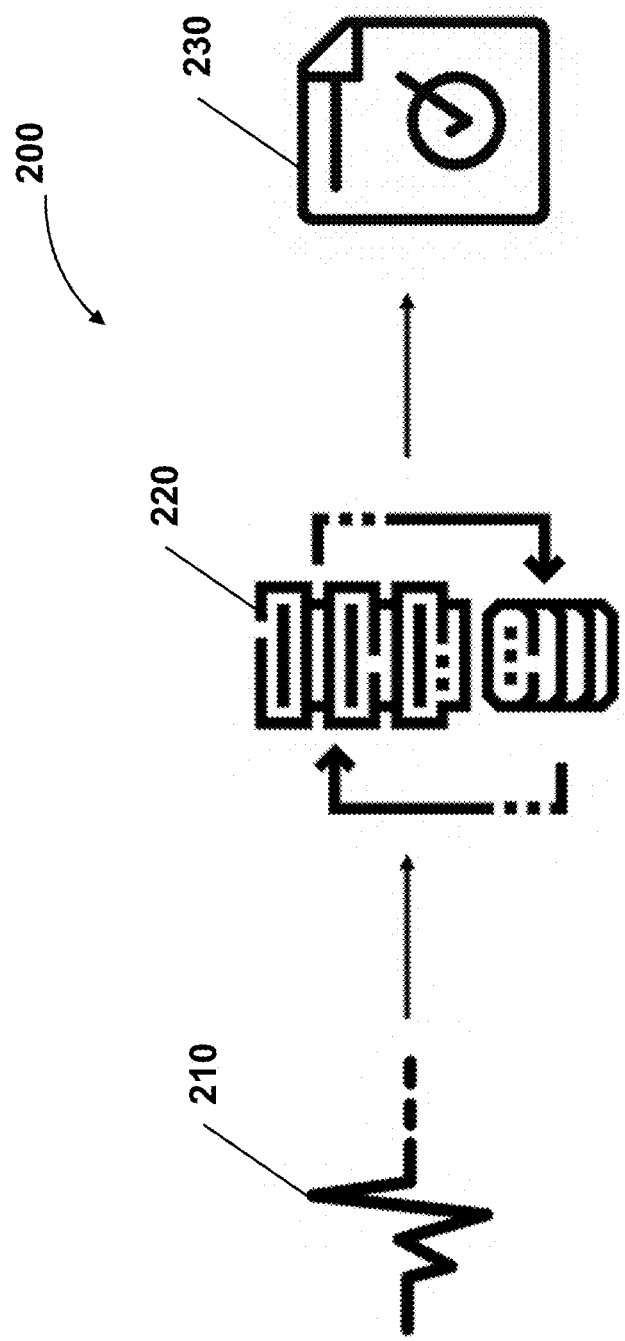
FIG. 2 is a schematic diagram illustrating an example system 200 for classifying a tympanic membrane, in accordance with some embodiments.

FIG. 2 is a schematic diagram illustrating an example system 200 for classifying a tympanic membrane, in accordance with some embodiments. System 200 may comprise one or more datasets 210 received from an interrogation system. The one or more datasets 210 may be stored in a memory of the system 200. System 200 may comprise a classifier model 220 operable to classify a tympanic membrane based on the one or more datasets 210 and output a classification 230. The classification 230 may comprise one or more of a state, a condition, or a mobility metric of the tympanic membrane. An output of the classifier model (e.g., a classification) may be generated. The classification may comprise information about the TM mobility, which can aid the physician in their diagnosis of OM infection or direct diagnosis of the patient's disease state.

For example, disclosed herein is a system for classifying a tympanic membrane. The system may comprise: a computing system comprising a memory, the memory comprising instructions for classifying the tympanic membrane, wherein the computing system is configured to execute the instructions to at least: receive from an interrogation system, one or more datasets relating to the tympanic membrane; determine a set of parameters from the one or more datasets, wherein at least one parameter of the set of parameters is related to a dynamic property of the tympanic membrane; and output a classification of the tympanic membrane based on a classifier model derived from the set of parameters, wherein the classification comprises a state, a condition, or a mobility metric of the tympanic membrane. Embodiments, variations, and examples of a computing device of the system for classifying a tympanic membrane is described elsewhere herein for example with respect to the section "Digital Processing Device" and FIG. 10 described therein.

Interrogation System

Figure 3:
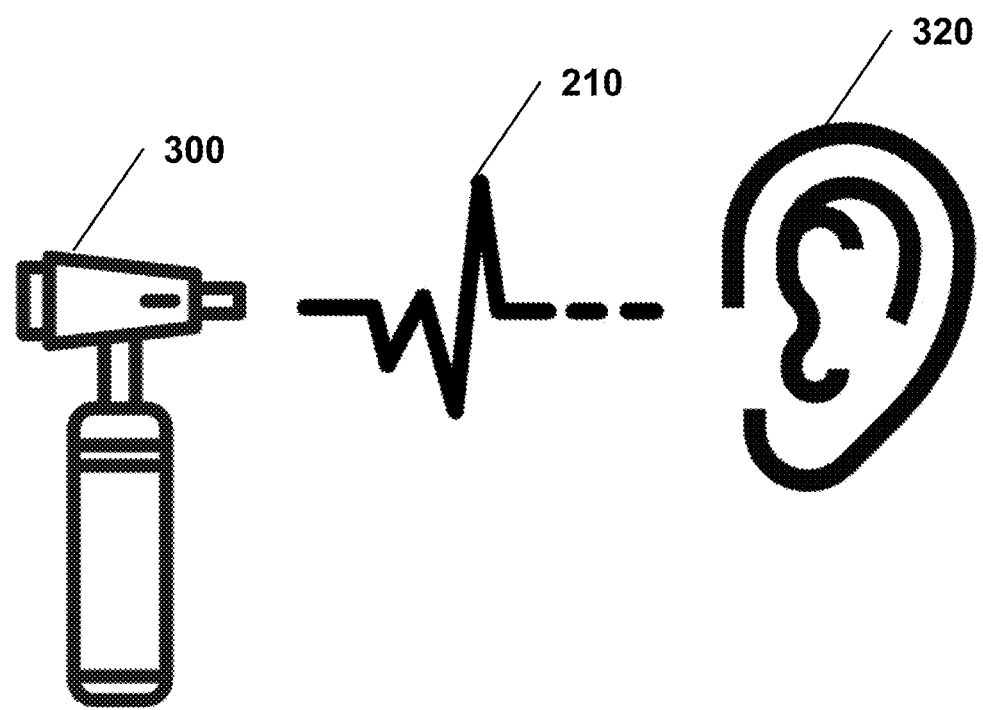
FIG. 3 is a schematic diagram illustrating an example of an interrogation system as disclosed herein.

FIG. 3 is a schematic diagram illustrating an example of an interrogation system 300 as disclosed herein. An interrogation system 300 as disclosed herein may collect one or more datasets 210 relating to the biological membrane (e.g., a tympanic membrane) of a subject 320, as disclosed herein. The one or more datasets relating to the tympanic membrane may comprise data relating to physical characteristics of the biological membrane (e.g., a tympanic membrane) to be characterized. In some examples, the interrogation system may comprise an imaging system. In some examples, the interrogation system does not comprise an imaging system. The interrogation system may collect ultrasound data, for example, reflected ultrasound data. The interrogation system may collect optical coherence tomography data. The interrogation may collect infrared data. The interrogation system may collect optical data. The interrogation system may collect data in response to a pneumatic excitation. The interrogation system may collect datasets relating to a membrane movement, for example, in response to a pneumatic excitation. A pneumatic excitation may comprise a pressure excitation, such as an air puff. The interrogation system may measure a pressure in an ear canal as a function of applied pressure. In an example, an interrogation system may measure pressure within the ear canal following a pneumatic excitation.

Any example or combination of examples of an interrogation system as disclosed herein may be used independently or in combination to provide datasets from which to generate parameters to include in a classifier model as disclosed herein. For example, any example or combination of examples of an interrogation system as disclosed herein may be used independently or in combination as inputs into a machine learning algorithm to provide classification outputs.

An interrogation system as disclosed herein may be remote from a classification system disclosed herein. An interrogation system may collect one or more datasets (e.g. data), which may be sent to a classification system as disclosed herein. In some cases, one or more datasets may be received from a remote server. However, in some cases, an interrogation system may be local to a classification system as disclosed herein. For example, a classification system may be a part of an onboard logic on a processor of a classification system, such as on a logic within an ultrasound tympanoscope.

In some cases, the interrogation system does not comprise an imaging system. For example, the interrogation system may comprise an ultrasound system. The ultrasound system may collect an ultrasound dataset, for example doppler ultrasound data. In some cases, the interrogation system collects frequency dependent data, for example, frequency dependent optical coherence tomography data, an absorption spectrum, depth dependent ultrasound tomography data, etc. The ultrasound data may comprise data from a pneumatic ultrasound tympanoscope.

The interrogation system may comprise ultrasound data. The ultrasound data may comprise amplitude mode (a-mode) ultrasound data. The ultrasound data may comprise 2-dimensional (b-mode) ultrasound data. The ultrasound data may comprise m-mode (motion mode) ultrasound data. The ultrasound data may comprise Doppler ultrasound data. The ultrasound data may comprise ultrasound m-mode phase at fixed gate depths vs time. The ultrasound data may comprise m-mode amplitude at fixed gate depths vs time.

In some examples, an interrogation system comprises an imaging system. An imaging system may collect one or more datasets comprising one or more images of the tympanic membrane. In an example, the images may comprise optical images, such as from a camera. In an example, the images may comprise ultrasound images. The images may comprise optical coherence tomography images. An imaging system may comprise any other imaging modality such as magnetic resonance imaging (MRI) or computed tomography (CT) or positron emission tomography (PET) or a combination of imaging modalities. Any of the image modalities may, optionally, be used with a pneumatic excitation. For example, an image may be collected in response to a pneumatic excitation. A number of images may be collected before and after a pneumatic excitation. The one or more images may comprise ultrasound images. The one or more ultrasound images comprise images from a pneumatic ultrasound tympanoscope. The one or more ultrasound images may be measured in response to a pneumatic excitation. In an example, an interrogation system may measure dynamic visual movement of the tympanic membrane using a CCD camera. Optical image dataset in response to a pneumatic excitation may comprise optical integrated image intensity vs time wave form. Optical image dataset in response to a pneumatic excitation may comprise cone of light intensity vs time wave form. Optical image dataset in response to a pneumatic excitation may comprise cone of light position vs time waveform. Optical image dataset in response to a pneumatic excitation may comprise an image sharpness index vs time waveform.

In an example, an interrogation system as disclosed herein may comprise an embodiment, variation, or example of the methods and systems disclosed in U.S. Pat. No. 7,771,356 and U.S. Patent Publication Nos. 2019/0365292, 2018/0310917, and 2017/0014053, which are each incorporated herein by reference in their entirety. Methods and systems for obtaining information regarding the motion of a tympanic membrane using ultrasound echo signals as disclosed in the incorporated references may be used to generate one or more parameters related to a dynamic property of the tympanic membrane. A system for measuring ultrasound echo signal may induce motion of the tympanic membrane by applying a systematic pressure pulse and then extracting Doppler shift signals from ultrasound waves to analyze displacement of the TM and/or categorize viscosity of ear effusion.

In an example, an interrogation system as disclosed herein may comprise an embodiment, variation, or example of the methods and systems disclosed in commonly assigned U.S. Patent Publication No. 2019/0200873 and U.S. Patent Publication No. 2017/0360302, each of which is incorporated herein by reference in its entirety. Methods and systems for characterizing a membrane using optical coherence tomography (OCT) as disclosed in U.S. Patent Publication No. 2019/0200873 and U.S. Patent Publication No. 2017/0360302 may be used to generate one or more parameters related to a dynamic property of the tympanic membrane. For example, a dynamic property of the tympanic membrane may comprise a phase delay or a time delay in the reflected optical signal in response to an applied pneumatic excitation. OCT may be used to collect depth dependent data related to the tympanic membrane. OCT may be used to collect frequency dependent data, such as wavelength of absorption of a membrane or a fluid adjacent a membrane.

The interrogation system may collect data in response to a pneumatic excitation. The interrogation system may collect data relating to a membrane movement, for example, in response to a pneumatic excitation. A pneumatic excitation may comprise a pressure excitation, such as an air puff. A pneumatic excitation may change a response of a membrane to ultrasound excitation. For example, a pneumatic excitation may cause a membrane to deflect which may change a phase of the reflected ultrasound relative to a membrane that was not exposed to the pneumatic excitation. A deflection of the membrane may comprise a damped harmonic motion. This motion may be affected by changes in the elasticity of the membrane. A change in the membrane elasticity may occur, for example, if water, bacterial growth, or other foreign material is adjacent the membrane.

In some examples, a pneumatic excitation may generate a movement of the surface or membrane during an interval of time. This interval may be coincident with acoustic wave delivered by an ultrasound transmitter to the surface or membrane. A pneumatic excitation may be continuous, may be pulsed, etc. The ultrasound reflected from the surface may be received at a transducer. A transducer may be the same transducer that generated the incident acoustic wave. A displacement of the surface or membrane may be related to a phase change in the received signal when compared to the transmit signal. A movement of the membrane may affect a phase change in the received ultrasound. A displacement may vary with time. An analysis of the temporal displacement of the surface or membrane, as measured by the phase shifts of the reflected ultrasound in response to the pneumatic excitation coupled to the surface or membrane may be used to determine the mechanical characteristics of the surface or membrane.

An analysis of the temporal information may be used in combination with the temporal displacement measured from templates of other membrane responses to create a comparison. An analysis of the temporal information may be used in combination with other metrics associated with the delay in an amplitude of reflected ultrasound, which characterizes the response of the surface or membrane. The mechanical characteristics measured may include ductility, elasticity, hardness, etc. A non-contact measurement of the mechanical properties of a surface or alternatively a fluid below the surface of a membrane may be determined.

In some embodiments, an elasticity of a surface may be measured. The phase and/or amplitude of the reflected ultrasound from the membrane may be analyzed to produce an elasticity metric. The elasticity measurement may characterize a series of measurements in response to an applied excitation. The elasticity metric may be derived from the response of the surface and may provide an indication of one or more of several different phenomena. For example, the elasticity metric may indicate whether a surface adjacent to a membrane has a gaseous boundary or fluid boundary. For example, a membrane may move less, move more slowly, and or not move at all if the membrane has a fluid boundary. In an example, the elasticity metric may indicate, for the case of characterizing a fluid behind the membrane fluid boundary, the extent or a characteristic of the fluid. In some examples, the elasticity metric may be used to measure the characteristics of an elastic fluid with or without hysteresis of response. In a fluid with a hysteresis response, the fluid may exhibit an offset in displacement response, or "memory," such that the response behavior in one direction is similar to the response behavior in the opposite direction, but only after traveling a particular displacement distance. For a hysteresis response, it may be necessary to characterize the linear behavior of the response after a particular measured displacement associated with the hysteresis of the system. A fluid elasticity metric may be determined from the characteristic response of the surface or membrane to the surface excitation and reflected ultrasound characterization.

In some embodiments, a surface deflection may be estimated. For example, the estimate of surface deflection may be derived from a measured estimate of velocity, acceleration, or any other metric associated with deflection over time. For example, a displacement of the surface will result in a shortened path from the transducer to the surface, and the reflected signal from the surface back to the transducer will return with a phase shift. The phase shift of the reflected ultrasound relative to an excitation thus confers information about an amount of deflection. With an estimate of the force applied by the excitation, an estimate of the elasticity of the membrane can be estimated.

In an example, the excitation is a step or impulse response with a rising edge, falling edge, or impulsive excitation. The impulse excitation starts an oscillating deflection of the membrane. The reflected ultrasound can be measured from the time of excitation through the damping period of the oscillation of the membrane. In some embodiments, an estimate of position, elasticity, or viscosity may be performed by examination of a ringdown characteristic. For example, the ringdown characteristic may comprise at least one of an exponential decay time or a ring cycle interval or frequency, such as the decomposition of a response into a ringdown characteristic, such as:

$$\phi(t)=e_{-t/\tau}\cos(2\pi ft)$$

where:
  $\phi(t)$ is the captured phase for a series of measurements;
  $\tau$ is the exponential decay coefficient;
  f is the ring cycle frequency; and
  t is time.

The damping constant of the oscillator may relate to energy lost from the membrane into the surrounding environment. In an example, if the membrane is adjacent to a fluid, the fluid may damp the oscillation of the membrane. The viscosity of the fluid may relate to the damping of the oscillator. The ring cycle frequency may relate to the restoring constant of the elastic membrane. The restoring constant may be related to the elasticity of the membrane. The restoring constant may be related to the viscosity of a fluid adjacent the membrane. The ring cycle frequency may be higher the lower the viscosity of a fluid adjacent the membrane.

Each excitation event may start a new deflection of the membrane. For example, an impulse excitation may pull the membrane in or push the membrane out for a limited period of time. For example, a square wave excitation may pull the membrane in or push the membrane out for a longer time. For example, a sine wave or other more complex excitation may be applied and the observed ringdown at the transducer may be a cross-correlation of the excitation field with the responding field. A pneumatic excitation may be applied at a frequency of less than 100 kHz, less than 1 kHz, less than 100 Hz, less than 10 Hz, less than 1 Hz, or less, or within a range given by any two the preceding values. A pneumatic excitation may be applied at a frequency greater than 1 Hz, greater than 10 Hz, greater than 100 Hz, greater than 1 kHz, greater than 100 kHz or more, or within a range given by any two the preceding values. A pneumatic excitation may be applied within a range between 10 Hz and 100 Hz.

Figure 4:
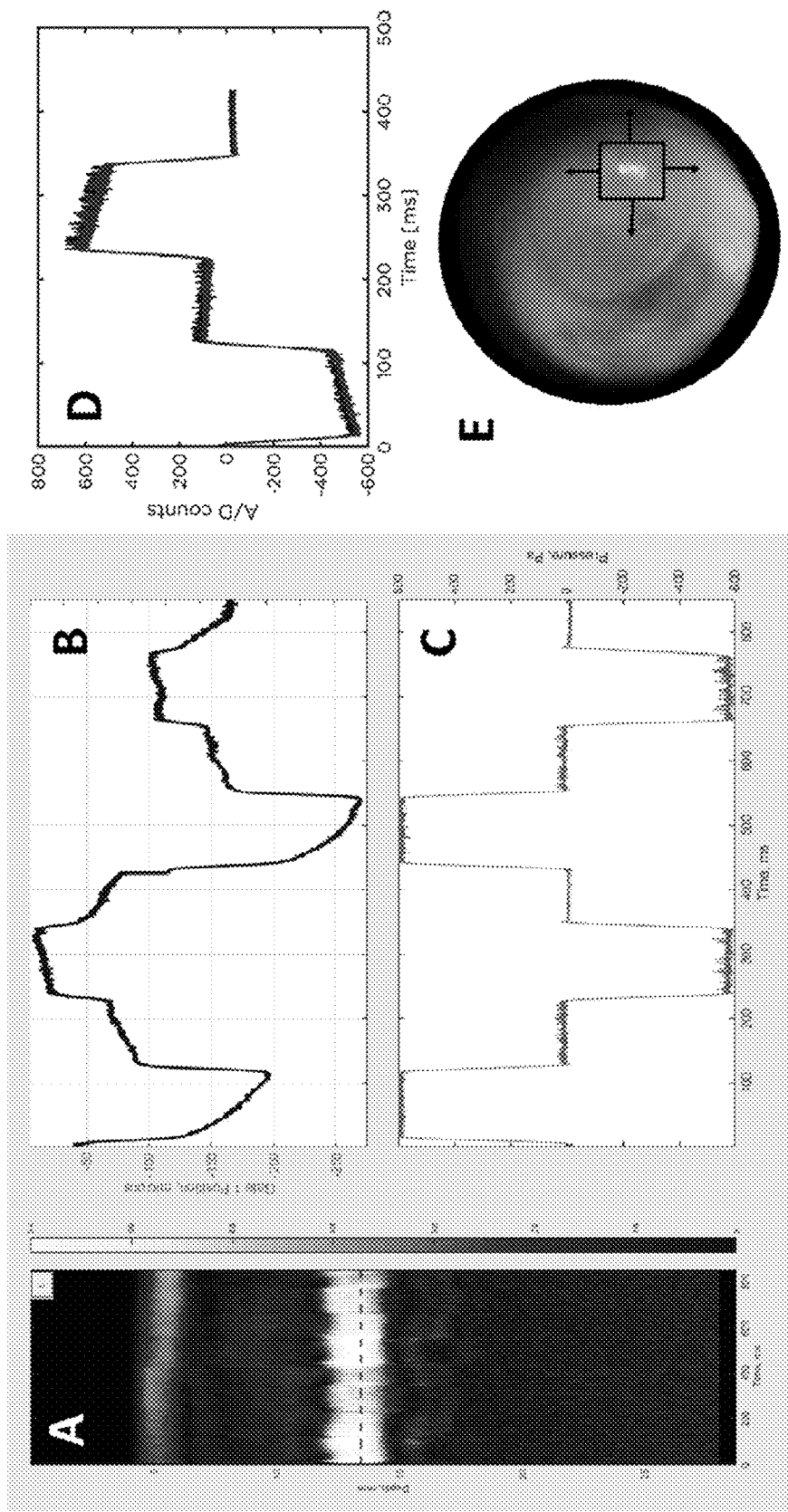
FIG. 4 illustrates example datasets provided by an interrogation device of the present disclosure.

FIG. 4 illustrates example datasets provided by an interrogation device of the present disclosure. At part A, FIG. 4 shows an intensity scale of m-mode ultrasound signal. Part A characterizes the position, of the moving tympanic membrane over a specified time range using the ultrasound measurements during the time course of application of a pressure pulse is applied. The horizontal time scale of part A is the same scale as in parts B, C and D (where Part D is abbreviated in its time extent compared to parts B and C). At part B, FIG. 4 shows a plot of a horizontal slice of the heatmap from part A (indicated by the dashed line). Whereas Part A shows the signal amplitude at all depths, Part B shows membrane positional changes based on signal phase changes over time. Part B indicates the tympanic membrane position with respect to the measured time. At part C, FIG. 4 shows applied pressure pulses over the same time range in part B. At part D, FIG. 4 shows measurements of the pressure within the ear canal during the pressure pulses spanning the first half of the time scale in part C. The measurements of pressure within the ear canal during the second half of the time scale of part C are plotted as a second curve in part D, translated in time to overlap the data from the first half. These sensed pressure profiles in Part D are very close in value and difficult to distinguish from each other, indicating very similar motions of the tympanic membrane when the pressure stimulus is repeated. At part E, FIG. 4 shows an example optical image recorded by a CCD camera, where dynamic movement of the white area, i.e., cone of light, (highlighted by the black box with arrows) during pressure pulses indicates mobility of the TM.

Taken together, FIG. 4 shows that as pressure pulses are applied (C), the generated and transformed ultrasound signals provide detailed information about the tympanic membrane position (A and B) and unique pressure and optical responses from image (D) and (E), respectively. The information contained within these measurements may be used to generate a set of parameters for training a classifier model, such as a machine learning model to output a classification.

Model Parameters

A set of parameters may be derived from the one or more datasets. At least one parameter of the set of parameters may be related to a dynamic property of the tympanic membrane. A set of parameters may also include parameters which relate to a static feature of the tympanic membrane (e.g. a parameter not related to membrane motion). A set of parameters may include parameters related to membrane motion and parameters not related to membrane motion. A set of parameters may include static parameters and dynamic parameters. A set of parameters may include one or more ultrasound features, one or more pressure features, and/or one or more optical features. A set of parameters or a subset of the set of parameters may be used as inputs into a classifier model, such as a trained machine learning algorithm. The classifier model may output a classification. The classification may include a mobility output. The classification may include a disease state.

At least one parameter of the set of parameters may be related to a dynamic property of the tympanic membrane. A dynamic property of the tympanic membrane may change with time. For example, a dynamic property of the tympanic membrane may change with time in response to a pneumatic excitation, for example, an air puff or a puff of a gas. A non-exhaustive list of potential parameters related to a dynamic property are as follows: an indication of a membrane movement or a membrane mobility; a minimum or maximum displacement of the tympanic membrane; an outlier displacement; a difference or a ratio between a minimum and a maximum displacement; a slope of a displacement or a slope of a difference or a ratio between a minimum and a maximum displacement with respect to a pressure of a pneumatic excitation; a response of a measured pressure versus an applied pressure; a visual movement of the tympanic membrane in response to a pneumatic excitation; one or more statistical components generated from singular value decomposition, principal component analysis, and K-means clustering; and ultrasound pulse echo amplitude or ultrasound echo phase or a derivative thereof or a moving average thereof. A dynamic parameter may be derived from a normalized or averaged dynamic property of the tympanic membrane in response to a dynamic excitation, such as a normalization or average of a parameter listed above.

Table 1 shows an example list of parameters relating to a dynamic property of the tympanic membrane. The displacement of the tympanic membrane in response to an applied pneumatic excitation may be measured by the method of FIG. 4. Alternatively, a displacement of the tympanic membrane in response to a pneumatic excitation may be measured by optical coherence tomography.

A parameter relating to a dynamic property of the tympanic membrane may comprise a minimum or maximum displacement of the tympanic membrane. The absolute distance that a tympanic membrane moves may vary by patient. Typically, greater displacement may relate to higher mobility, while lower displacement may relate to lower mobility. These displacements may be indicative of the various classifications. For example, a low mobility may relate to a viscous fluid behind the membrane.

A parameter relating to a dynamic property of the tympanic membrane may comprise an outlier displacement. In some instances, a measured displacement may be so large or small as to move outside of a measurement range of the ultrasound device. This "outlier" displacement may be treated as a categorical yes/no feature. A large outlier may be typically indicative of a highly mobile tympanic membrane. A small outlier may be typically indicative of a highly immobile tympanic membrane.

A parameter relating to a dynamic property of the tympanic membrane may comprise a difference or a ratio between a minimum and a maximum displacement. A difference between a minimum and a maximum displacement may relate to a static retraction or distension of the tympanic membrane. A static retraction or distension may be measured by measurement of the relationship between the distance traveled by the membrane during + and − pressure pulses. A distended membrane (toward the interrogation device) may be indicated by more mobility during a positive pressure cycle and less mobility during a negative pressure cycle. A retracted membrane may be indicated by less mobility during a positive pressure cycle and more mobility during a negative pressure cycle. Such a measurement may be used to extract a static membrane parameter, e.g. a distended membrane or a retracted membrane.

A parameter relating to a dynamic property of the tympanic membrane may comprise a variation of the displacement features include normalizing any of the displacement features by the amplitude of the measured pressure pulse and any other linear or non-linear transformation using displacement and measured pressure as the movement will be at least partially dependent on the pressure stimuli applied. This metric may be bi-directional, e.g. characterization of tympanic membrane mobility may be more complete knowing the metric under a positive pressure stimulus as well as under a negative pressure stimulus.

A parameter relating to a dynamic property of the tympanic membrane may comprise a slope of a displacement, a slope of a difference between a minimum and a maximum displacement with respect to a pressure of a pneumatic excitation, or a slope of a ratio between a minimum and a maximum displacement with respect to a pressure of a pneumatic excitation. After the membrane is displaced by the pressure pulse, the velocity with which it returns to its original position may be indicative of membrane mobility. A velocity may be measured by a derivative of the displacement measurement described herein. A second or higher order derivative may also be utilized. A damping coefficient of ring down feature, as described herein may also relate to a restoring force of the membrane.

A parameter relating to a dynamic property of the tympanic membrane may comprise a response of a measured pressure versus an applied pressure. A measured pressure that is less than the applied pressure may indicate a membrane mobility. It could also indicate failure of the instrument seal, which would allow for errors in the procedure to be identified. A parameter relating to a dynamic property of the tympanic membrane may comprise a slope of a pressure response. The slope of the pressure may directly correlate with tympanic membrane mobility.

The tympanic membrane movement may be viewed via CCD camera during pressure stimuli. These visual movements and displacements (rate, magnitude) may be transformed into input parameters or features for training a classifier. For example, a user (e.g. a medical profession) may indicate an observation of a membrane mobility. A user may indicate that a membrane is qualitatively mobile or immobile. A user may indicate a mobility on a 0-4 point scale. For example, after pressure is applied in the ear canal, a normal tympanic membrane may move briskly and be categorized as 4+, while a partially or fully impaired tympanic membrane may be categorized as 3+, 2+, 1+, or no mobility to represent decreasing degrees of mobility on an ordinal scale. For example, a medical provider may indicate a snappiness of the tympanic membrane, e.g., qualitatively how quickly the membrane snaps back in response to an applied excitation. The pressure assessment may be performed by clinicians during pneumatic otoscopy.

Other parameters may be derived from other types of ultrasound signals that may arise due to different pre-processing of the ultrasound signal, including but not limited to: bandpass filters at different frequencies, different sequences of pulses and measurements, transformations of the (I,Q) Doppler signal, and data processing steps. Various non-limiting examples include: a bandpass filter may be applied in the "fast time domain" of ultrasound signal capture, to remove noise artifacts that are out of the pass band of the ultrasound transducer and thereby improve signal-to-noise ratio; the phase of the (I,Q) Doppler signal at the depth of the tympanic membrane can be integrated to derive a parameter of membrane displacement versus time; the parameter of displacement versus time may be parsed to reveal response during change in external ear canal stimulus pressure, and evaluated for slope (snappiness or sluggishness) and position at beginning and end of pressure stimulus change (informing total change in position); a Hilbert transform may be used to assess the amplitude of the ultrasound reflection from the tympanic membrane, and can be evaluated at the times of stimulus pressure changes to detect change in cone of light orientation under pressure stimulus as further indication of tympanic membrane mobility; membrane motion directionality can be evaluated as a qualification of a priori understanding, for example, under a decrease in pressure in the external ear canal, the tympanic membrane may move toward the ultrasound transducer, and vice versa under an increase in pressure in the external ear canal; signal to noise ratio of the reflection from the tympanic membrane can be evaluated to qualify the resulting mobility measurement as valid or not; and multiple adjacent gates may be identified which cover a depth range broader than the tympanic membrane signal, and may be monitored concurrently so as to best keep track of the tympanic membrane signal during the time frame that it is positioned in front of the transducer, and evaluate mobility from the best of the gate depths having a qualified tympanic membrane signal.

A parameter relating to a dynamic property of the tympanic membrane may be derived from Doppler ultrasound data. For example, the Doppler signal of the tympanic membrane as a function of time may include ultrasound echo amplitude and ultrasound echo phase. These parameters may be dependent on a specific pulse-echo gate depth. A parameter related to ultrasound echo amplitude may comprise data relating to tympanic membrane acoustic cross section and direction of the tympanic membrane surface normal. A parameter related to ultrasound echo phase may comprise a time derivative of the ultrasound echo phase. The ultrasound echo phase may be proportional to membrane velocity.

A parameter relating a dynamic property of the tympanic membrane may comprise features derived from principal component analysis, K-means, or similar cluster algorithms on any of the above datasets. For example, any linear or non-linear transformations of the static data (e.g. principal component analysis, K-means clustering) to reduce collinearity of features or cluster similar groups of samples based on their respective features may be used to extract one or more parameters. PCA and K-means may be used on the various datasets to create parameters. PCA and K-Means may be tried when collinearity between features creates redundant information in the dataset. PCA and K-means may reduce variance in predication or may provide parameters which improve accuracy. In the case of PCA, the principle components may be used as training features by themselves or in combination with non-transformed features. Any number of principle components may be chosen (e.g. only the top 2-3 or N number of components up until an explained variance was met such as 95%). For the K-means clustering, a feature may be derived, such as "cluster," where a categorical training feature comprised of the cluster group that each sample falls into may be used as a parameter in a training model.

Generating additional features with respect to time, including moving averages and exponential moving averages over different window lengths.

TABLE 1

Example parameters related to dynamic properties of the tympanic membrane

| | |
|---|---|
| Minimum and maximum displacement of the tympanic membrane | Ultrasound |
| Outlier displacement outside measurable range | Ultrasound |
| Difference and ratio between minimum and maximum displacements | Ultrasound |
| Normalizing displacement by applied pressure | Ultrasound + Pressure |

TABLE 1-continued

Example parameters related to dynamic properties of the tympanic membrane

| | |
|---|---|
| Slope of the displacement at the start, during or immediately following the end of a pressure pulse | Ultrasound + Pressure |
| Measured response of the pressure versus the applied pressure | Pressure |
| Slope of the measured pressure response | Pressure |
| Visual movement of the "bright" location during systematic pressure pulses | Optical + Pressure |
| Linear or non-linear transformations | All |
| Moving averages with time | All |

A set of parameters may include parameters which relate to a static property of the membrane. For example, an interrogation system which produces an optical measurement may allow for the extraction of parameters based on visual features. Visual indicators of otitis media may include the coloration, transparency, and/or bulge. Other static parameters may include color, opacity, translucency, and position. A visual feature from an optical measurement may be indicated by a user and may be represented by a parameter, for example, visible bulge or no visible bulge.

In another example, parameters which relate to a static position property of the tympanic membrane may be derived from optical coherence tomography methods. For example, a parameter may be related to a depth characteristic of the tympanic membrane. For example, an ear contains a low-viscosity infectious effusion, an initial peak of the tympanic membrane optical coherence tomography signal may generate an axial region of extended reflection with an amplitude that drops from optical attenuation of the reflected signal. For example, an ear contains a bacterial infection, a bacterial film may be present on the opposite surface of the tympanic membrane, which may produce a greater axial extent of reflection, followed by a high scattering coefficient and corresponding increased attenuation. For example, a parameter may be related to a wavelength of an absorbing feature of the tympanic membrane. If a tympanic membrane is found to absorb at a wavelength which corresponds to a bacterial effusion or a viral effusion or no effusion, a wavelength of absorption or an identity of an absorption feature may comprise a parameter of the set of parameters. Classification Methods and systems of the present disclosure may output a classification (e.g. an output) of the tympanic membrane. The classification may be based on a classifier model as disclosed herein, which classifier may be a machine learning algorithm. A set of parameters or a subset of the set of parameters may be used as inputs into a classifier model, such as a trained machine learning algorithm. The classifier model may output a classification. The classification may include a mobility output. The classification may include a disease state. The classification may comprise one or more of a state, a condition, or a mobility metric of the tympanic membrane. An output of the classifier model may be generated. The output may comprise information about the TM mobility, which can aid the physician in their diagnosis of otitis media infection or direct diagnosis of the patient's disease state.

Figure 5:
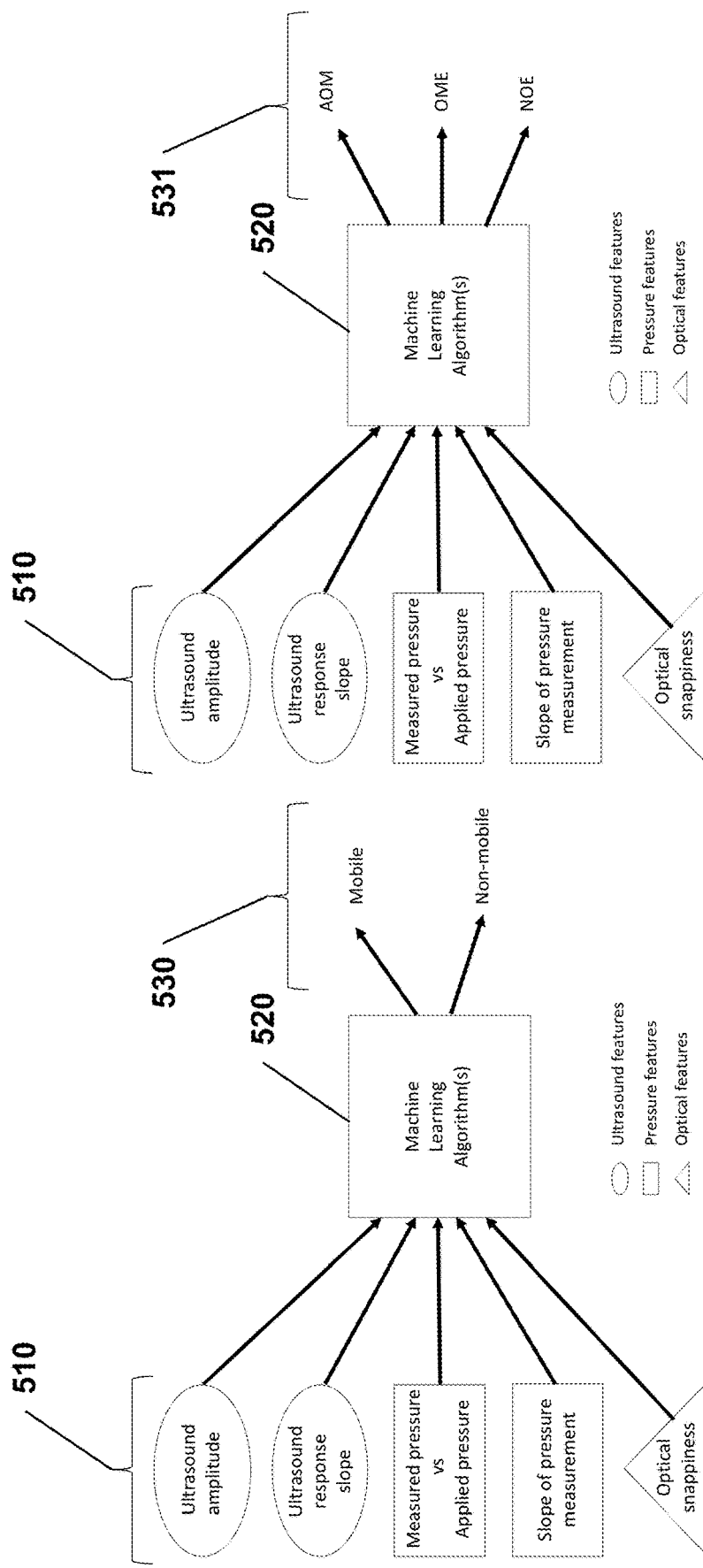
FIG. 5A and FIG. 5B are schematic diagrams of sets of parameters derived from pressure, ultrasound, and optical measurements which may comprise inputs to classifier model to output a classification, in accordance with some embodiments.

FIG. 5A and FIG. 5B are schematic diagrams of sets of parameters derived from pressure, ultrasound, and optical measurements which may comprise inputs 510 to classifier model 520 to output a classification, in accordance with some embodiments. As shown in FIG. 5A, an amplitude of reflected ultrasound, slope of the ultrasound response after a pressure excitation, measured pressure versus applied pressure, slope of the pressure response, and optical snappiness may comprise inputs to a classifier. The classifier may output a mobility metric 530. As shown in FIG. 5A, a mobility metric 530 may comprise a binary classification, such as mobile or non-mobile. As shown in FIG. 5B, an amplitude of reflected ultrasound, slope of the ultrasound response after a pressure excitation, measured pressure versus applied pressure, slope of the pressure response, and optical snappiness may comprise inputs to a classifier. The classifier may output a state or condition 531, such as acute otitis media, otitis media with effusion, and no effusion, as shown.

In some cases, the classification may comprise a mobility metric of the tympanic membrane. A mobility metric may comprise one or more of a binary classification, an ordinal output, a categorical ordinal output, or a continuous numeric value. A classification may include various forms of tympanic membrane information, which information may be provided to a medical provider (e.g., a physician). A classification may be based on one or more of ultrasound, pressure, and optical measurement features.

In some examples, a classification comprises a categorical readout. A categorical readout may comprise an indication of a degree of membrane mobility as at least one of highly mobile, moderately mobile, semi mobile, or non-mobile. For example, a categorical classification may comprise highly mobile, moderately mobile, semi mobile, or non-mobile. In some examples, a categorical readout comprises a binary classification. A binary classification may comprise mobility or no-mobility. A binary classification may comprise normal mobility or abnormal mobility. In an example, a simple classification may be a binary classifier where the binary choice based on the max probability of either "mobile" or "non-mobile" is displayed to the physician.

In some examples, a classification comprises a categorical ordinal classification. A categorical-ordinal classification may comprise a 0-4+ scale as describe herein above. In another example, a categorical-ordinal output may comprise a 0-10 point scale, e.g. 10.0 is highly mobile, 5.0 is somewhat mobile and 0 is non-mobile (or the reverse). A user may indicate that a membrane is qualitatively mobile or immobile. A user may indicate a mobility on a 0-4 point scale. For example, after pressure is applied in the ear canal, a normal tympanic membrane may move briskly and be categorized as 4+, while a partially or fully impaired tympanic membrane may be categorized as 3+, 2+, 1+, or no mobility to represent decreasing degrees of mobility on an ordinal scale. The pressure assessment may be performed by clinicians during pneumatic otoscopy.

In some examples, a classification comprises a continuous numeric output which comprises one or more of a measurement membrane displacement, a speed of membrane movement, or a speed of membrane recovery. In some examples, an ordinal readout comprises a numerical scale relating to a degree of membrane mobility. A continuous metric may comprise a numerical scale with decimated increments. In an example of a continuous numeric output, continuous variable regression algorithms may be used to generate continuous predictions, e.g. a percent likelihood of a particular state or condition. In some examples, the state or condition may be normalized to some value or scale. For example, a continuous metric may be normalized such that maximum value is 10 and minimum is zero, where 10 is relates to a highly mobile membrane and 0 relates to an immobile membrane, or vice versa.

In some examples, multi-class classifications may be used. For example, a binary classification (e.g., mobile or not mobile) may be determined, and if non-mobile is most likely, then the various degrees of non-mobility may be classified (e.g. 0 vs 1+ vs 2+ vs 3+ on the 4-point scale). In another example, the classification may comprise an expected probability of each possible category. An expected probability may comprise a maximum probability chosen as a classification displayed to a medical provider. For example, a probability may be calculated using the softmax function or strategies such as one-vs-rest classification.

A classification may indicate a state or condition of the tympanic membrane to a user (e.g. a medical provider). In some cases, a classification may comprise a state or a condition of the tympanic membrane. The state or condition of the tympanic membrane may comprise one or more of acute otitis media, acute otitis media with effusion, middle ear effusion, a bacterial infection, a viral infection, no effusion, and an unknown classification. A classification that an ear exhibits acute otitis media may include detection of the presence of effusion and characterization of the type of effusion as one of serous, mucoid, purulent, or combinations of these. In acute otitis media, the middle ear effusion may be induced by infective agents and may be thin or serous with viral infection and thicker and purulent with bacterial infection.

Classifier Model

Figure 6:
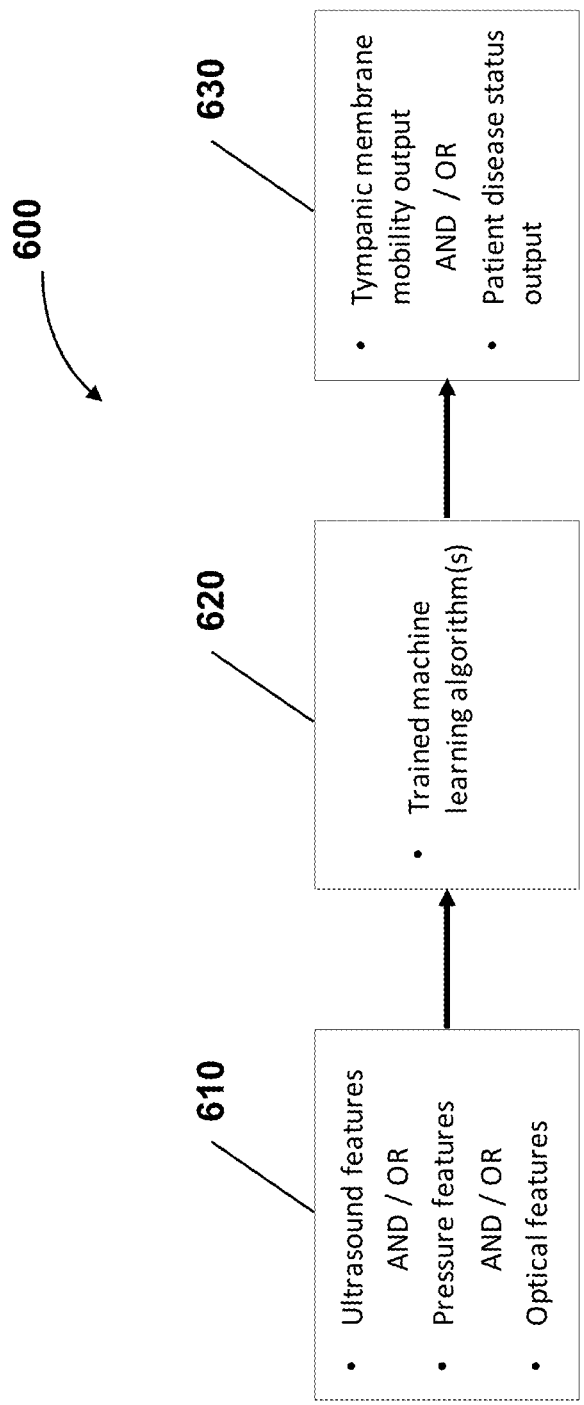
FIG. 6 is a schematic diagram illustrating an example 600 of a classifier model comprising a machine learning algorithm, in accordance with some embodiments.

FIG. 6 is a schematic diagram illustrating an example 600 of a classifier model comprising a machine learning algorithm, in accordance with some embodiments. A classifier model may be generated based on the set of parameters 610. A set of parameters 610 may include ultrasound features and/or pressure features and/or optical features. For example, the set of parameters may comprise inputs to a classifier model and a classification may be an output of the classifier model. The classifier model may output a classification 630. The classification may include a mobility output. The classification may include a disease state.

The classifier model may comprise a machine learning algorithm 620. For example, the machine learning algorithm may comprise one or more of linear regressions, logistic regressions, classification and regression tree algorithms, support vector machines (SVMs), naive Bayes, K-nearest neighbors, random forest algorithms, boosted algorithms such as XGBoost and LightGBM, neural networks, convolutional neural networks, and recurrent neural networks. The machine learning algorithm may be a supervised learning algorithm, an unsupervised learning algorithm, or a semi-supervised learning algorithm.

Machine learning algorithms may be used in order to make predictions using a set of parameters. One class of machine learning algorithms, artificial neural networks (ANNs), may comprise a portion of the classifier model. For example, feedforward neural networks (such as convolutional neural networks or CNNs) and recurrent neural networks (RNNs) may be used. A neural network binary classifier may be trained by comparing predictions made by its underlying machine learning model to a ground truth. An error function calculates a discrepancy between the predicted value and the ground truth, and this error is iteratively backpropagated through the neural network over multiple cycles, or epochs, in order to change a set of weights that influence the value of the predicted output. Training ceases when the predicted value meets a convergence condition, such as obtaining a small magnitude of calculated error. Multiple layers of neural networks may be employed, creating a deep neural network. Using a deep neural network may increase the predictive power of a neural network algorithm. In some cases, a machine learning algorithm using a neural network may further include Adam optimization (e.g., adaptive learning rate), regularization, etc. The number of layers, the number of nodes within the layer, a stride length in a convolutional neural network, a padding, a filter, etc. may be adjustable parameters in a neural network.

Additional machine learning algorithms and statistical models may be used in order to obtain insights from the parameters disclosed herein. Additional machine learning methods that may be used are logistic regressions, classification and regression tree algorithms, support vector machines (SVMs), naive Bayes, K-nearest neighbors, and random forest algorithms. These algorithms may be used for many different tasks, including data classification, clustering, density estimation, or dimensionality reduction. Machine learning algorithms may be used for active learning, supervised learning, unsupervised learning, or semi-supervised learning tasks. In this disclosure, various statistical, machine learning, or deep learning algorithms may be used to generate an output based on the set of parameters.

A machine learning algorithm may use a supervised learning approach. In supervised learning, the algorithm can generate a function or model from training data. The training data can be labeled. The training data may include metadata associated therewith. Each training example of the training data may be a pair consisting of at least an input object and a desired output value. A supervised learning algorithm may require the user to determine one or more control parameters. These parameters can be adjusted by optimizing performance on a subset, for example, a validation set, of the training data. After parameter adjustment and learning, the performance of the resulting function/model can be measured on a test set that may be separate from the training set. Regression methods can be used in supervised learning approaches.

In some embodiments, the supervised machine learning algorithms can include but not being limited to neural networks, support vector machines, nearest neighbor interpolators, decision trees, boosted decision stump, boosted version of such algorithms, derivatives versions of such algorithms, or their combinations. In some embodiments, the machine learning algorithms can include one or more of: a Bayesian model, decision graphs, inductive logic programming, Gaussian process regression, genetic programming, kernel estimators, minimum message length, multilinear subspace learning, naive Bayes classifier, maximum entropy classifier, conditional random field, minimum complexity machines, random forests, ensembles of classifiers, and a multicriteria classification algorithm.

A machine learning algorithm may use a semi-supervised learning approach. Semi-supervised learning can combine both labeled and unlabeled data to generate an appropriate function or classifier.

In some embodiments, a machine learning algorithm may use an unsupervised learning approach. In unsupervised learning, the algorithm may generate a function/model to describe hidden structures from unlabeled data (i.e., a classification or categorization that cannot be directed observed or computed). Since the examples given to the learner are unlabeled, there is no evaluation of the accuracy of the structure that is output by the relevant algorithm. Approaches to unsupervised learning include: clustering, anomaly detection, and neural networks.

A machine learning algorithm may use a reinforcement learning approach. In reinforcement learning, the algorithm can learn a policy of how to act given an observation of the world. Every action may have some impact in the environment, and the environment can provide feedback that guides the learning algorithm.

Although the machine learning algorithms discussed previously may generate much more complex relationships between the input features and the output labels, a few simple examples of a relational algorithm are shown by the illustrative decision trees in FIG. 7.

Figure 7A:
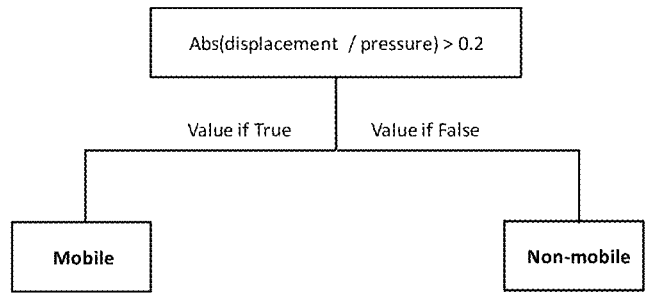
FIG. 7A, FIG. 7B, and FIG. 7C are schematic diagrams illustrating example decision trees which may be generated by a machine learning algorithm, in accordance with some embodiments.
Figure 7B:
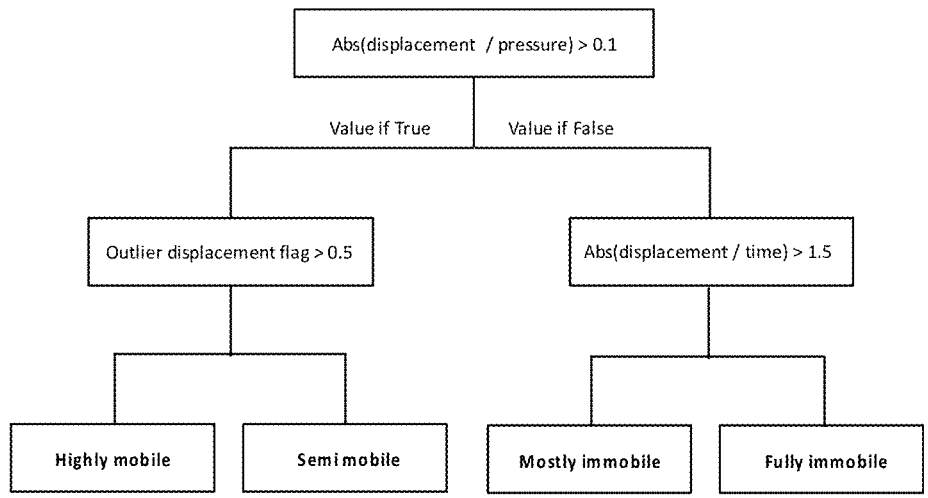
Figure 7C:
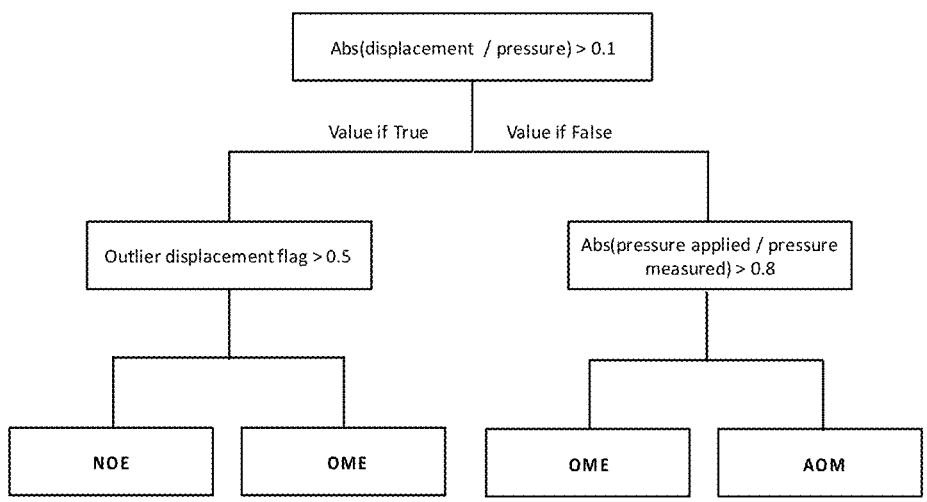

FIG. 7A, FIG. 7B, and FIG. 7C are schematic diagrams illustrating example decision trees which may be generated by a machine learning algorithm, in accordance with some embodiments. In some embodiments, the machine learning algorithm builds a decision tree based on the set of parameters. The decision tree may comprise a threshold value of a parameter within the set of parameters. The threshold value may determine which branch of the tree a dataset should be classified into. A decision tree may comprise the greatest information gain at the top nodes of the tree. A decision tree may be built, in part, by searching for the most informative nodes (e.g., parameters) for a given dataset.

In some examples, a decision tree is pruned. Pruning may comprise reducing the number of parameters within a set of a parameters to a subset of most relevant parameters. The subset of parameter may be the minimum number of parameters to classify of a dataset within a specified sensitivity or specificity, for example, 90% sensitivity or specificity. In some embodiments, a decision tree comprises J48, C4.5, or ID3. In some embodiments, a decision tree comprises ADA-Boost or DecisionStump.

As shown in FIG. 7A, a first example tree comprises a single parameter (e.g., the absolute value of the displacement). If the parameter is greater than the threshold value of 0.2 mm, the membrane is classified as mobile. If the parameter less than the threshold value of 0.2 mm, the membrane is classified as non-mobile.

As shown in FIG. 7B, a second example tree comprises three parameters (e.g., the absolute value of the displacement with a fixed pressure stimulus amplitude, the absolute value of the displacement with fixed time measurement window duration, and outlier displacement). The classification of the model relates to a mobility of the tympanic membrane. If the absolute value of the displacement with fixed pressure stimulus amplitude is greater than the threshold value of 0.1 and the outlier displacement is greater than 0.5, the membrane is highly mobile. If the absolute value of the displacement with fixed pressure stimulus amplitude is greater than the threshold value of 0.1 and the outlier displacement is less than 0.5, the membrane is semi mobile. If the absolute value of the displacement with fixed pressure stimulus amplitude is less than the threshold value of 0.1 and the absolute value of the displacement with fixed time measurement window duration is greater than 1.5, the membrane is mostly immobile. If the absolute value of the displacement with fixed pressure stimulus amplitude is less than the threshold value of 0.1 and the absolute value of the displacement with fixed time window duration is less than 1.5, the membrane is fully immobile.

As shown in FIG. 7C, a third example tree comprises three parameters (e.g., the absolute value of the displacement with a fixed pressure stimulus amplitude, the absolute value of the displacement with fixed time measurement window duration, and outlier displacement). The classification of the model relates to state or condition of the tympanic membrane. If the absolute value of the displacement with a fixed pressure stimulus amplitude is greater than the threshold value of 0.1 and the outlier displacement is greater than 0.5, the membrane is characterized as having no effusion. If the absolute value of the displacement with a fixed pressure stimulus amplitude is greater than the threshold value of 0.1 and the outlier displacement is less than 0.5, the membrane is characterized as having otitis media with effusion. If the absolute value of the displacement with fixed pressure stimulus amplitude is less than the threshold value of 0.1 and the absolute value of the displacement with fixed time window duration is greater than 1.5, the membrane is characterized as having otitis media with effusion. If the absolute value of the displacement with a fixed pressure stimulus amplitude is less than the threshold value of 0.1 and the absolute value of the displacement with fixed time window duration is less than 1.5, the membrane is characterized as having acute otitis media.

Training a Computer Implemented Classifier

Figure 8:
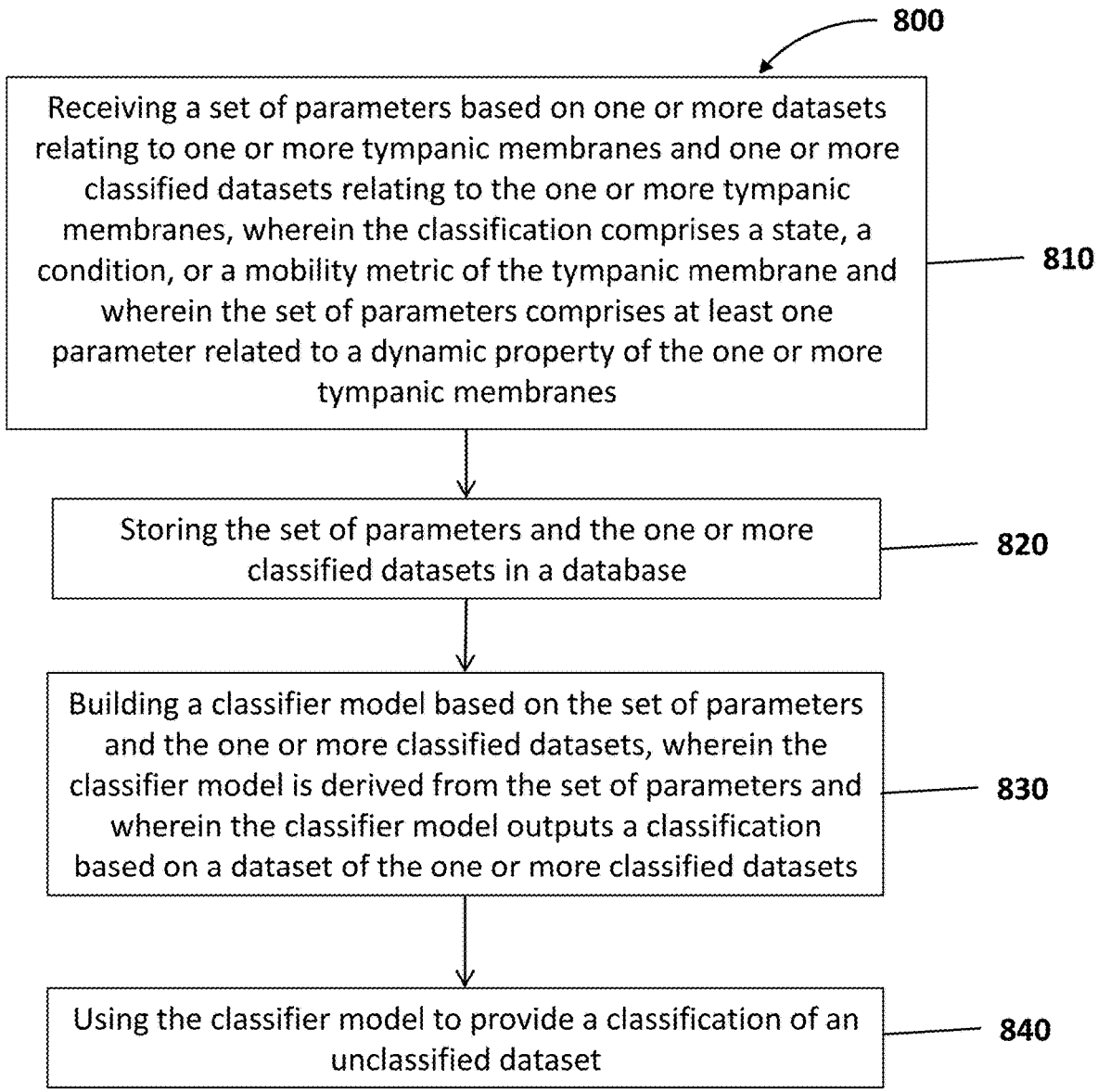
FIG. 8 is a flowchart of an example method of training a computer-implemented classifier, in accordance with some embodiments.

FIG. 8 shows a flowchart of an example method of training a computer-implemented classifier, in accordance with some embodiments. At an operation 810, the method 800 may comprise receiving a set of parameters based on one or more datasets relating to one or more tympanic membranes and one or more classified datasets relating to the one or more tympanic membranes. The classification may comprise a state, a condition, or a mobility metric of the tympanic membrane and wherein the set of parameters comprises at least one parameter related to a dynamic property of the one or more tympanic membranes. At an operation 820, the method 800 may comprise storing the set of parameters and the one or more classified datasets in a database. At an operation 830, the method 800 may comprise building a classifier model based on the set of parameters and the one or more classified datasets. The classifier model may be derived from the set of parameters and wherein the classifier model outputs a classification based on a dataset of the one or more classified datasets. At an operation 840, the method 800 may comprise using the classifier model to provide a classification of an unclassified dataset.

In some cases, the method further comprises updating the database based on a second one or more classified datasets. In some cases, the method further comprises updating the classifier model based on the second one or more classified datasets. The method may further comprise using the classifier model to provide a classification of an unclassified dataset by the method for classifying a tympanic membrane describe herein. The classifier may be continually updated. For example, the method may use an online gradient descent or stochastic gradient descent method to continually update the model parameters for improved detection. In some cases, a classifier may be update with every dataset. A classifier may be updates with recent samples in batches.

Although the above operations show a method 800 of training a computer-implemented classifier, in accordance with some embodiments, a person of ordinary skill in the art will recognize many variations based on the teachings described herein. The steps may be completed in any order. Steps may be added or deleted. Some of the steps may comprise sub-steps. Many of the steps may be repeated as often as beneficial to the method of manufacture.

One or more steps of the method 800 may be performed with the circuitry as described herein, for example, one or more of the digital processing device or processor or logic circuitry such as the programmable array logic for a field programmable gate array. The circuitry may be programmed to provide one or more steps of the method 800, and the program may comprise program instructions stored on a computer readable memory or programmed steps of the logic circuitry such as the programmable array logic or the field programmable gate array, for example. Embodiments, variations, and examples of a digital processing device operable to perform one or more steps of the method 800 is described elsewhere herein for example with respect to the section "Digital Processing Device" and FIG. 10 described therein.

Figure 9:
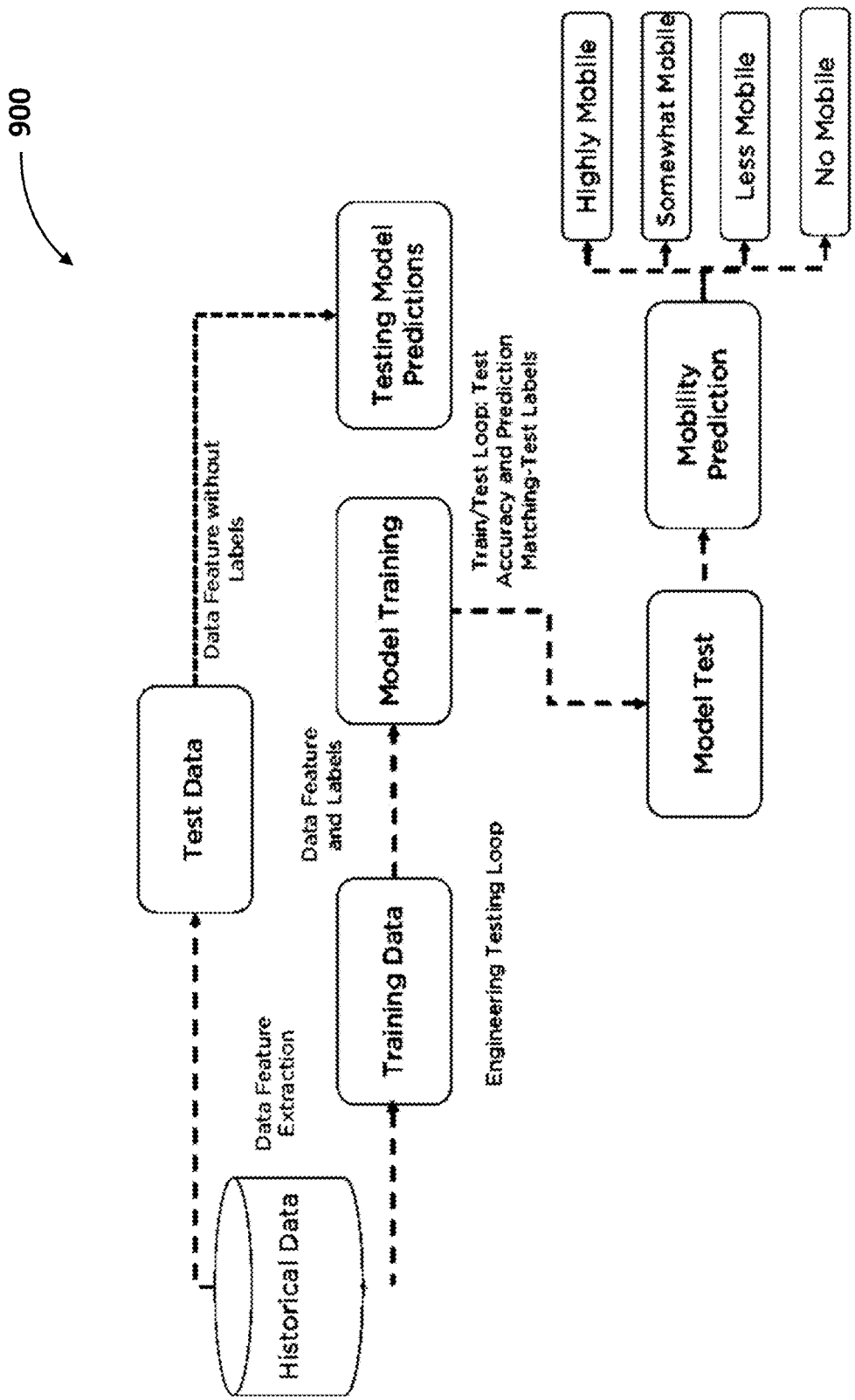
FIG. 9 is a schematic diagram illustrating an example of a system for training a computer implemented classifier.

FIG. 9 is a schematic diagram illustrating an example of a system 900 for training a computer implemented classifier, in accordance with some embodiments. The system of FIG. 9 may comprise an example of a system operable to perform the method 800 as shown in FIG. 8. The system 900 may comprise one or more classified datasets (e.g., historical data). The one or more classified datasets may comprise one or more datasets relating to one or more tympanic membranes. The classified datasets may comprise data with a known classification. For example, the classified datasets may comprise dataset from tympanic membranes that have been biopsied. The classified datasets may have an associated set of parameters, including a least one parameter based on a dynamic property of the tympanic membrane. The classified datasets may have an associated classification. In some cases, a set of parameters (e.g., features) may be extracted from the one or more classified datasets.

In the lower loop of the system 900, all or a portion of the one or more classified datasets may be used as training data. The set of parameters for the classified datasets may be used as part of a guided learning algorithm to train a classifier model to find the classification. For example, all or a portion of the classified data may be used as a training dataset for a guided learning algorithm.

As shown in the upper loop of the system 900, a portion of the classified datasets may be reserved as a validation dataset (e.g., test data). The validation data may have a set of established classification, for example, by experiment. The validation dataset may be used to test predictions of the classifier model. The validation dataset may be used to validate a model trained on the training dataset. The training data may be used as a part of an engineering test loop. For example, a model or a set of models (e.g., an "ensemble") may be determined using a validation procedure wherein the model is trained on a subset of the available data (e.g., the training data) and then used to predict the remaining subset of available data (e.g., the test data). An accuracy metric (e.g., root-mean-squared error for numerical data, precision and recall for categorical data, area under receiver-operation curve (AUC), etc.) may be defined to categorize how accurate a given model is for the provided dataset. In some examples, over- or under-sampling (e.g. Synthetic Minority Over-Sampling Technique (SMOTE)) may be used during model training as part of model building.

A risk of machine learning models to fail to generalize to data that the model has never encountered before may be mitigated by using as large of a representative training dataset as possible. Additionally, utilizing techniques such as hyperparameter tuning with cross-validation to maximize model generalization may improve model generalization. Briefly, hyperparameter tuning may change aspects of a given model to prevent either bias (i.e., under-fitting) or variance (i.e., over-fitting) with respect to the training and validation data. Additionally, cross-validation may be used to consecutively train on different subsets of data (e.g., K-Fold and Leave-one-out) and the accuracy predictions generated from each subset may be averaged to create an overall accuracy metric for a given model.

A trained classifier model may be then be subjected to testing on an unclassified dataset. For example, an unclassified dataset may comprise one or more tympanic membranes which are not in the set of classified data. The classifier model may be used to generate a classification based on the set of parameters extracted from the unclassified dataset. The classifier model may be used to classify a membrane as, for example, one of highly mobile, somewhat mobile, less mobile, or not mobile.

Figure 10:
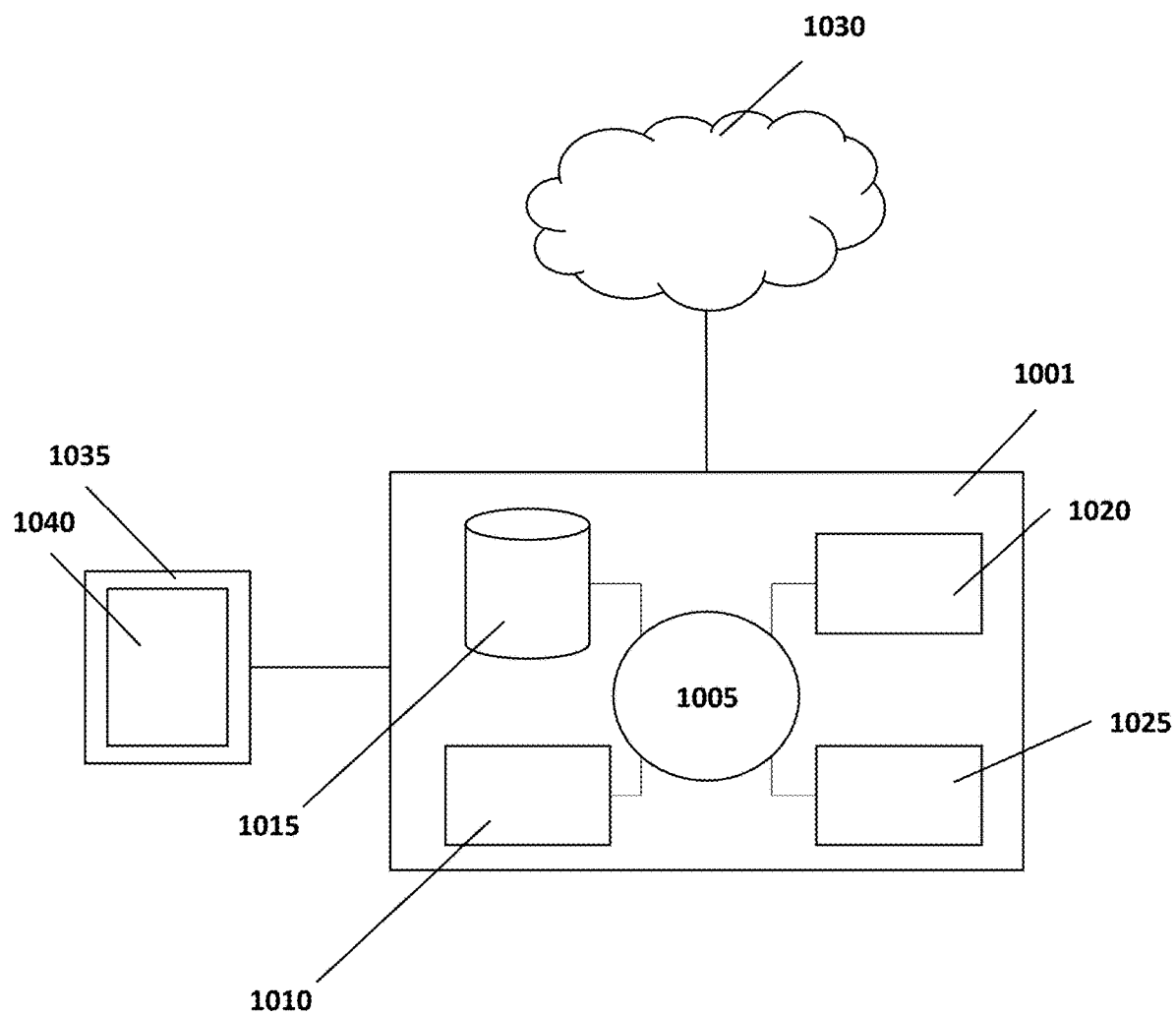
FIG. 10 is a schematic diagram illustrating of an example system for classifying a tympanic membrane comprising a digital processing device and a display visible to a user, in accordance with some embodiments.

A system for training a computer-implemented classifier may comprise embodiments, variations, and examples of a digital processing device described elsewhere herein for example with respect to the section "Digital Processing Device" and FIG. 10 described therein.

Digital Processing Device

In some embodiments, devices, systems, and methods of use thereof described herein include a digital processing device or use of the same. For example, a digital processing device may be used to control various aspects of the devices and methods disclosed herein. For example, a digital processing device may be used to perform a method of classifying a tympanic membrane. A digital processing device may comprise a computing system, for example, the computing system comprising a memory, the memory comprising instructions for classifying the tympanic membrane. The digital processing device may be configured to perform one or more steps of the method for classifying a tympanic membrane. The digital processing device may be configured to perform one or more steps of the method 100 or the method 800, as disclosed herein. A digital processing device may be configured to control an interrogation system, such as any example, variation, or example of an interrogation system as disclosed herein. A digital processing device may receive and/or retrieve one or more datasets from an interrogation system. A digital processing device may comprise database management systems for the one or more datasets. A digital processing device may perform one or more steps for training a computer implemented classifier, as described herein.

In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device may be optionally connected a computer network. In further embodiments, the digital processing device is optionally connected to the internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Referring to FIG. 10, in a particular embodiment, an example digital processing device 1001 is programmed or otherwise configured control to or to implement the systems and methods for classifying a tympanic membrane and the systems and methods for training a computer implemented classifier as described herein. The device 1001 may regulate various aspects of the systems and methods for classifying a tympanic membrane and systems and methods for training a computer implemented classifier of the present disclosure, such as, for example, performing processing steps. In this embodiment, the digital processing device 1001 includes a central processing unit (CPU, also "processor" and "computer processor" herein) 1005, which may be a single core or multi core processor, or a plurality of processors for parallel processing. The digital processing device 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 may be a data storage unit (or data repository) for storing data. The digital processing device 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the device 1001, can implement a peer-to-peer network, which may enable devices coupled to the device 1001 to behave as a client or a server.

Continuing to refer to FIG. 10, the CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and write back. The CPU 1005 can be part of a circuit, such as an integrated circuit. One or more other components of the device 1001 can be included in the circuit. In some cases, the circuit is an application specific integrated circuit (ASIC) or a field programmable gate array (FPGA).

Continuing to refer to FIG. 10, the storage unit 1015 can store files, such as drivers, libraries and saved programs. The storage unit 1015 can store user data, e.g., user preferences and user programs. The digital processing device 1001 in some cases can include one or more additional data storage units that are external, such as located on a remote server that is in communication through an intranet or the Internet. The digital processing device 1001 can communicate with one or more remote computer systems through the network 1030. For instance, the device 1001 can communicate with a remote computer system of a user.

Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1001, such as, for example, on the memory 1010 or electronic storage unit 1015. The machine executable or machine-readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The digital processing device 1001 can include or be in communication with an electronic display 1035 that comprises a user interface (UI) 1040. Examples of UI's include, without limitation, a graphical user interface (GUI) and web-based user interface. In some cases, electronic display 1035 may be connected to the computer system 1001 via a network, e.g., via network 1030.

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of datasets from an interrogation system, storage classified datasets, determination of parameters from the one or more datasets, storage of parameters associated with classified datasets, etc. In various embodiments, suitable databases include, by way of non-limiting examples, relational databases, non-relational databases, object-oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

What is claimed is:

1. A method for classifying a tympanic membrane, the method comprising:
   receiving, from an interrogation system, one or more datasets relating to the tympanic membrane;
   determining a set of parameters from the one or more datasets, wherein at least one parameter of the set of parameters is related to a dynamic property or a static position of the tympanic membrane;
   outputting a classification of the tympanic membrane based on a classifier model derived from the set of parameters, wherein the classification comprises one or more of a state, a condition, or a mobility metric of the tympanic membrane; and
   generating one or more of an ordinal readout, a categorical readout, or a continuous numeric output of tympanic membrane mobility.

2. The method of claim 1, wherein the interrogation system comprises an imaging system, and wherein the one or more datasets comprises one or more images of the tympanic membrane.

3. The method of claim 1, wherein the classifier model comprises a machine learning algorithm.

4. The method of claim 3, wherein the machine learning algorithm comprises one or more of linear regressions, logistic regressions, classification and regression tree algorithms, support vector machines (SVMs), naive Bayes, K-nearest neighbors, random forest algorithms, boosted algorithms such as XGBoost and LightGBM, neural networks, convolutional neural networks, and recurrent neural networks.

5. The method of claim 3, wherein the machine learning algorithm is a supervised learning algorithm, an unsupervised learning algorithm, or a semi-supervised learning algorithm.

6. The method of claim 2, wherein the one or more images of the tympanic membrane comprises one or more ultrasound images.

7. The method of claim 6, wherein the one or more ultrasound images comprise images from a pneumatic ultrasound tympanoscope or wherein the one or more ultrasound images are measured in response to a pneumatic excitation.

8. The method of claim 2, wherein the one or more images of the tympanic membrane comprise one or more optical coherence tomography images or one or more optical images.

9. The method of claim 2, wherein the at least one parameter related to the dynamic property or a static position of the membrane is in response to a pneumatic excitation.

10. The method of claim 9, wherein the pneumatic excitation comprises a puff of gas.

11. The method of claim 9, wherein the pneumatic excitation has a frequency greater than 10 Hz.

12. The method of claim 1, wherein the dynamic property of the tympanic membrane comprises one or more of:
  an indication of a membrane movement or a membrane mobility;
  a minimum or maximum displacement of the tympanic membrane;
  an outlier displacement;
  a difference or a ratio between a minimum and a maximum displacement;
  a slope of a displacement or a slope of a difference or a ratio between a minimum and a maximum displacement with respect to a pressure of a pneumatic excitation;
  a response of a measured pressure versus an applied pressure;
  a visual movement of the tympanic membrane in response to a pneumatic excitation;
  one or more statistical components generated from singular value decomposition, principal component analysis, and K-means clustering; and
  ultrasound pulse echo amplitude or ultrasound echo phase or a derivative thereof or a moving average thereof.

13. The method of claim 12, wherein the dynamic property of the tympanic membrane is normalized with respect to a pressure of a pneumatic excitation.

14. The method of claim 1, wherein an ordinal readout comprises a numerical scale relating to a degree of membrane mobility.

15. The method of claim 1, wherein a categorical readout comprises an indication of a degree of membrane mobility as at least one of highly mobile, moderately mobile, semi mobile, or non-mobile or wherein a categorical readout comprises a binary classification.

16. The method of claim 1, wherein a continuous numeric output comprises one or more of a measurement membrane displacement, a speed of membrane movement, or a speed of membrane recovery.

17. The method of claim 1, wherein the state or condition of the tympanic membrane comprises one or more of acute otitis media, acute otitis media with effusion, middle ear effusion, chronic otitis media, chronic suppurative otitis media, a bacterial infection, a viral infection, no effusion, and an unknown classification.

18. The method of claim 1, wherein the one or more datasets comprise m-mode ultrasound datasets, infrared images, pneumatic datasets, or one or more optical images are taken in response to a pneumatic excitation.

19. The method of claim 1, wherein the static position comprises a distended membrane or a retracted membrane.

20. A system for classifying a tympanic membrane, the system comprising:
  a computing system comprising a memory, the memory comprising instructions for classifying the tympanic membrane, wherein the computing system is configured to execute the instructions to at least:
  receive from an interrogation system, one or more datasets relating to the tympanic membrane;
  determine a set of parameters from the one or more datasets, wherein at least one parameter of the set of parameters is related to a dynamic property or a static position of the tympanic membrane;
  output a classification of the tympanic membrane based on a classifier model derived from the set of parameters, wherein the classification comprises a state, a condition, or a mobility metric of the tympanic membrane; and
  generate one or more of an ordinal readout, a categorical readout, or a continuous numeric output of tympanic membrane mobility.

21. A non-transitory computer readable medium comprising machine-executable code that upon execution by a computing system implements a method for classifying a membrane, the method comprising:
  receiving from an interrogation system, one or more datasets relating to the tympanic membrane;
  determining a set of parameters from the one or more datasets, wherein at least one parameter of the set of parameters is related to a dynamic property or a static position of the tympanic membrane;
  outputting a classification of the tympanic membrane based on a classifier model derived from the set of parameters, wherein the classification comprises a state, a condition, or a mobility metric of the tympanic membrane; and
  generating one or more of an ordinal readout, a categorical readout, or a continuous numeric output of tympanic membrane mobility.

* * * * *